(12) United States Patent
Hill et al.

(10) Patent No.: US 8,883,184 B2
(45) Date of Patent: *Nov. 11, 2014

(54) METHODS AND COMPOSITIONS FOR REGENERATING CONNECTIVE TISSUE

(75) Inventors: Ronald Stewart Hill, Greenville, NC (US); Richard Chris Klann, Washington, NC (US); Francis V. Lamberti, Greenville, NC (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 809 days.

This patent is subject to a terminal disclaimer.

(21) Appl. No.: 12/356,195

(22) Filed: Jan. 20, 2009

(65) Prior Publication Data

US 2009/0124552 A1 May 14, 2009

Related U.S. Application Data

(62) Division of application No. 10/971,544, filed on Oct. 22, 2004, now abandoned.

(60) Provisional application No. 60/513,392, filed on Oct. 22, 2003.

(51) Int. Cl.
| | | |
|---|---|---|
| A61K 38/39 | (2006.01) | |
| A61L 27/26 | (2006.01) | |
| A61K 38/18 | (2006.01) | |
| A61L 26/00 | (2006.01) | |
| A61K 38/01 | (2006.01) | |
| A61L 27/48 | (2006.01) | |
| A61L 27/52 | (2006.01) | |
| A61K 35/32 | (2006.01) | |

(52) U.S. Cl.
CPC ............... *A61L 27/52* (2013.01); *A61L 27/26* (2013.01); *A61K 38/1875* (2013.01); *A61L 26/0052* (2013.01); *A61L 26/008* (2013.01); *A61L 2430/10* (2013.01); *A61K 38/014* (2013.01); *A61L 27/48* (2013.01); *A61L 26/0057* (2013.01); *A61K 35/32* (2013.01)
USPC ............ 424/423; 424/488; 514/1.1; 514/7.6; 514/8.1; 514/8.2; 514/8.5; 514/8.8; 514/8.9; 514/9.1; 514/9.6

(58) Field of Classification Search
None
See application file for complete search history.

(56) References Cited

U.S. PATENT DOCUMENTS

| | | | |
|---|---|---|---|
| 4,520,821 A | 6/1985 | Schmidt et al. | |
| 4,772,468 A | 9/1988 | Pfirrmann | |
| 5,290,558 A | 3/1994 | O'Leary et al. | |
| 5,303,718 A | 4/1994 | Krajicek | |
| 5,376,375 A | 12/1994 | Rhee et al. | |
| 5,470,911 A | 11/1995 | Rhee et al. | |
| 5,484,601 A | 1/1996 | O'Leary et al. | |
| 5,645,591 A | 7/1997 | Kuberasampath et al. | |
| 5,783,214 A | 7/1998 | Royer | |
| 5,800,541 A | 9/1998 | Rhee et al. | |
| 5,866,165 A | 2/1999 | Liu et al. | |
| 5,972,385 A | 10/1999 | Liu et al. | |
| 6,132,759 A | 10/2000 | Schacht et al. | |
| 6,160,084 A * | 12/2000 | Langer et al. | 528/272 |
| 6,261,587 B1 | 7/2001 | Usala | |
| 6,264,992 B1 * | 7/2001 | Voytik-Harbin et al. | 424/551 |
| 6,352,707 B1 | 3/2002 | Usala | |
| 6,391,052 B2 | 5/2002 | Buirge et al. | |
| 6,833,408 B2 | 12/2004 | Sehl et al. | |
| 2002/0176893 A1 | 11/2002 | Wironen et al. | |
| 2003/0032098 A1 | 2/2003 | Young et al. | |
| 2003/0147935 A1* | 8/2003 | Binette et al. | 424/423 |
| 2003/0220245 A1* | 11/2003 | Hubbell et al. | 514/12 |
| 2004/0091462 A1 | 5/2004 | Lin et al. | |
| 2004/0138128 A1* | 7/2004 | Lee et al. | 514/12 |
| 2005/0176620 A1* | 8/2005 | Prestwich et al. | 514/2 |

FOREIGN PATENT DOCUMENTS

WO    WO 03/072155 A1    9/2003

OTHER PUBLICATIONS

Boyan et al., "Role of Material Surfaces in Regulating Bone and Cartilage Cell Response," *Biomaterials*, 1996, pp. 137-146, vol. 17.
Griffon, "Evaluation of Osteoproductive Biomaterials: Allograft, Bone Inducing Agent, Bioactive Glass, and Ceramics," Academic Dissertation, 2002, Dept. of Clinical Veterinary Sciences, University of Helsinki, Finland, pp. 1-100.
Holmes, T., "Novel Peptide-Based Biomaterial Scaffolds for Tissue Engineering," *TRENDS in Biotechnology*, 2002, pp. 16-21, vol. 20 (1), Elsevier Science, Ltd.
Hutmacher, D., "Scaffolds in Tissue Engineering Bone and Cartilage," *Biomaterials*, 2000, pp. 2529-2543, vol. 21, Elsevier Science Ltd.
Jansson, K., et al., "A Biodegradable Collagen Membrane as a Dermal Template for Human in vivo Wound Healing," *Scand. J Plast. Reconstr. Hand Surg.*, 2001, pp. 369-375, vol. 35.
Kuijpers, A.J., et al., "In vivo Compatibility and Degradation of Crosslinked Gelatin Gels Incorporated in Knitted Dacron," *J. Biomed Mater Res.*, 2000, pp. 136-145, vol. 51.
Liu, L., et al., "An Osteoconductive Collagen/Hyaluronate Matrix for Bone Regeneration," *Biomaterials*, 1999, pp. 1097-1108, vol. 20, Elsevier Science Ltd.

(Continued)

*Primary Examiner* — Laura Schuberg
(74) *Attorney, Agent, or Firm* — Womble Carlyle Sandridge & Rice, LLP

(57) ABSTRACT

Connective tissue regenerative compositions and methods of repairing and regenerating connective tissue using such compositions are provided. The compositions generally comprise a bioactive hydrogel matrix comprising a polypeptide, such as gelatin, and a long chain carbohydrate, such as dextran. The hydrogel matrix may further include polar amino acids, as well as additional beneficial additives. Advantageously, the compositions include further components, such as osteoinductive or osteoconductive materials, medicaments, stem or progenitor cells, and three-dimensional structural frameworks. The compositions are useful for regenerating connective tissue, and can be administered to an area having injury to, or a loss of, connective tissue, such as bone, cartilage, tendon, and ligament.

37 Claims, 10 Drawing Sheets

(56) References Cited

OTHER PUBLICATIONS

Puleo, D.A., et al., "A Technique to Immobilize Bioactive Proteins, Including Bone Morphogenetic Protein-4 (BMP-4), on Titanium Alloy," *Biomaterials*, 2002, pp. 2079-2087, vol. 23, Elsevier Science Ltd.

Ulubayram, K., et al., "EGF Containing Gelatin-Based Wound Dressings," *Biomaterials*, 2001, pp. 1345-1356, vol. 22.

Yaylaoğlu, M.B., et al., "Development of a Calcium Phosphate-Gelatin Composite as a Bone Substitute and its Use in Drug Release," *Biomaterials*, 1999, pp. 711-719, vol. 20.

* cited by examiner

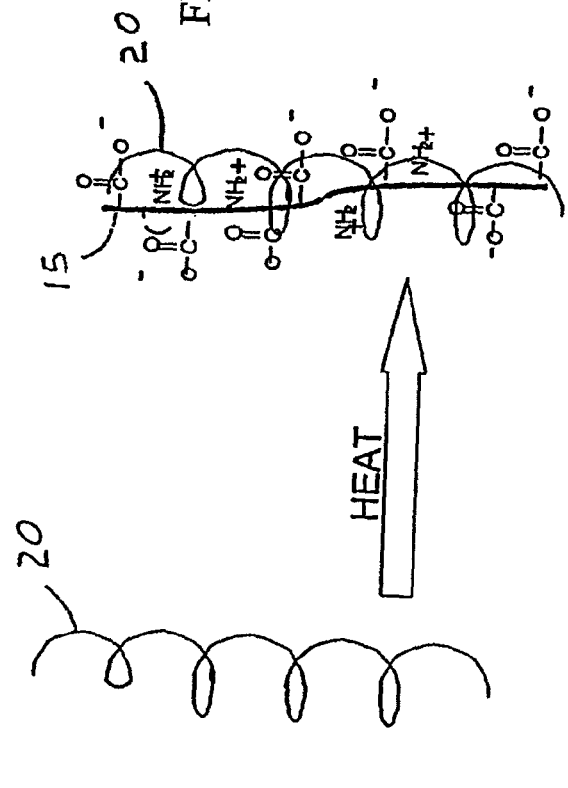
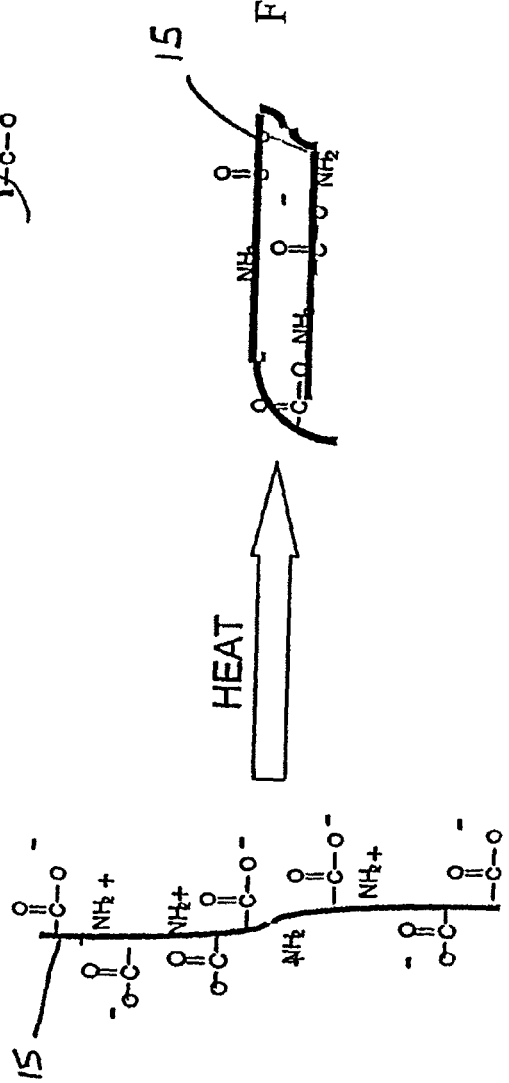

METHODS AND COMPOSITIONS FOR REGENERATING CONNECTIVE TISSUE

CROSS-REFERENCE TO RELATED APPLICATION

The present application is a division of U.S. patent application Ser. No. 10/971,544, filed Oct. 22, 2004 now abandoned, which claims the benefit of U.S. Provisional Patent Application Ser. No. 60/513,392, filed Oct. 22, 2003, both of which are hereby incorporated by reference for all purposes.

FIELD OF THE INVENTION

The present invention is related to methods and compositions for regenerating connective tissue, such as bone, cartilage, ligament, tendon, and the like. In particular, the invention is related to methods for regenerating connective tissue through application of a hydrogel matrix, wherein the matrix is comprised of a polypeptide, such as gelatin, and a long chain carbohydrate, such as dextran.

BACKGROUND OF THE INVENTION

Injuries to bone, such as partial or complete fracture, can be slow to heal, but such injuries generally heal on their own accord with external immobilization as needed, such as by applying a cast to the affected area. In more severe cases, more aggressive internal immobilization, such as permanently reconnecting the fractured bone with screws and/or metal plates, may be required. Regeneration of bone tissue over the relatively short distances generally present in bone fracture readily occurs in most healthy patients. Bone injuries beyond simple fractures, however, present greater challenges in treatment. Long segmental diaphyseal bone loss, for example, can result from multiple causes including high-energy trauma, such as blast injury, disease, such as osteomyelitis or osteonecrosis, or wide excision of malignant conditions, such as osteosarcoma. Such conditions often result in cavitation of the bone or complete loss of bone tissue across an extended length of the bone (i.e., a critical bone defect). Bone regeneration in these cases becomes increasingly challenging and sometimes impossible.

Many techniques have been used in an attempt to enhance bone growth. Most commonly, an attempt is made to replace the lost bone. Examples of such techniques include autologous vascularized bone grafts, massive allograft (generally from cadaver), and use of reabsorbable and non-reabsorbable artificial bone. Another method for promoting bone regeneration is through the introduction of osteoinductive bioactive factors, such as bone morphogenetic proteins (BMPs), platelet rich plasma (PRP), synthetic peptides, such as P-15 (Pepgen P-15™, Dentsply International, York, Pa.), and bone marrow aspirates. Such bioactive factors can be introduced into the area of bone loss through various vehicles. Mechanical methods, such as distraction osteogenesis, are also employed for promoting bone regeneration. Distraction osteogenesis is a process involving gradual, controlled displacement of surgically created fractures resulting in simultaneous expansion of soft tissue and bone volume.

A somewhat less invasive technique that is used most commonly for regenerating bone around teeth is known as "guided bone regeneration." As the tissue surrounding a bone almost always heals faster than the bone itself, the faster-healing tissue often expands into and fills the space where the bone is missing, hindering the bone regeneration. In guided bone regeneration, a biocompatible membrane is placed between the tissue and the bone acting as a barrier, which prevents growth of the tissue into the bone. Often, a bone graft is inserted under the barrier. The membranes are typically designed to dissolve away after several weeks.

A variation on this procedure is known as "protected bone regeneration" and is based on the theory that three prerequisites for bone healing are required: 1) adequate blood supply, 2) abundant bone forming cells, and 3) protected healing space. See, Holmes, R. E., Lemperle, S. M., and Calhoun, C. J., "Protected Bone Regeneration," *Scientific Data Series in Resorbable Fixation*, distributed by Medtronic Sofamor Danek, available on-line at http://www.macropore.com/pdf/Protected_Bone.pdf. Adequate blood supply is a known requirement for bone regeneration as it supplies the necessary oxygen and nutrients, as well as mesenchymal stem cells (the bone forming cells). As described above, the healing space of the bone must also be protected from the ingrowth of surrounding tissue. According to the above-noted publication, all of the stated prerequisites can be met through the use of a reabsorbable polymer protective sheet offering a physiologically balanced porosity for positive cellular exchange and the opportunity for vascular infiltration, while preventing interposition of adjacent soft tissues.

While there are several methods currently known, treatment of injury resulting in major bone loss remains a difficult clinical problem. Furthermore, approximately 10% of all long bone fractures are non-union fractures that do not heal spontaneously. Thus, there remains a need for methods for bone regeneration that are effective at promoting bone tissue growth and that are as non-invasive as possible.

SUMMARY OF THE INVENTION

It has been discovered that the matrix described herein is capable of successfully promoting regeneration of connective tissue. Surprisingly, the matrix is even useful for effecting bone regeneration in bone with defects that will not normally spontaneously heal. The present invention provides a method for connective tissue regeneration comprising administration of a bioactive hydrogel matrix into the site in need of connective tissue regeneration. As used herein, "bioactive" is intended to indicate the ability to facilitate a cellular or tissue response, such as, induction of vasculogenesis, promotion of cellular attachment to a scaffold material, and promotion of tissue regeneration.

In one aspect of the invention, there is provided a method for regenerating connective tissue. In one embodiment, the method comprises administering to a site in need of connective tissue regeneration a bioactive hydrogel matrix comprising a polypeptide and a long chain carbohydrate. The polypeptide can be selected from tissue-derived polypeptides or synthetic polypeptides. In one embodiment, the polypeptide is skin-derived gelatin. In another embodiment, the polypeptide is bone-derived gelatin. Exemplary long chain carbohydrates include polysaccharides and sulfated polysaccharides. In one embodiment, the long chain carbohydrate is dextran. The bioactive hydrogel matrix further comprises one or more components selected from the group consisting of polar amino acids, polar amino acid analogues or derivatives and divalent cation chelators, such as ethylenediaminetetraacetic acid (EDTA) or salts thereof.

The bioactive hydrogel matrix, as used in the above method, can further include one or more various structuring agents, medicaments, or other agents useful for facilitating or mediating connective tissue regeneration.

In one embodiment of the invention, the bioactive hydrogel matrix can further comprise at least one osteoinductive or osteoconductive material. In this embodiment of the invention, the method is particularly useful for regenerating bone; moreover, the use of osteoinductive or osteoconductive materials is not limited to bone regeneration.

In yet another embodiment of the invention, the bioactive hydrogel matrix further comprises at least one medicament. Any medicament recognizable by one of skill in the art as useful in the treatment of connective tissue injury, particularly in methods of regenerating connective tissue, could be used. For example, the medicaments can include antivirals, antibacterials, anti-inflammatories, immunosuppressants, analgesics, anticoagulants, or various wound healing promotion agents.

In one particular embodiment of the invention, the bioactive hydrogel matrix further comprises stem or progenitor cells, such as adipose-derived adult stem (ADAS) cells or mesenchymal stem cells. Such cells are known in the art as useful in various therapies due to their ability to differentiate into a number of cell types. ADAS cells in particular are known to differentiate into cell types including chondrocytes and osteoblasts.

In still another embodiment of the method of the invention, the bioactive hydrogel matrix is at least partially contained within a three-dimensional structural framework. Accordingly, the structural framework can be included with the bioactive hydrogel matrix prior to administration of the bioactive hydrogel matrix to the site in need of connective tissue regeneration. Alternatively, the structural framework can be formed around the site in need of connective tissue regeneration at the time of administration of the bioactive hydrogel matrix (i.e., formed shortly before or shortly after administration of the bioactive hydrogel matrix). The three-dimensional structural framework, therefore, includes any material capable of providing load-bearing structural support or anatomical space for cellular infiltration and includes, for example, a metal cage, a sintered ceramic framework, a collagen sponge, or allogenic or autologous bone. The structural framework can further include three dimensional structures prepared from polymeric materials, including biopolymers.

The bioactive hydrogel matrix can also be used in the method of the invention in a dehydrated form. In such form, the bioactive hydrogel matrix retains its beneficial properties yet can be stored and transported in a solid form, being capable of re-hydration for use in the method of the present invention. In one embodiment, the bioactive hydrogel matrix is administered in a dehydrated form such that body fluids re-hydrate the bioactive hydrogel matrix. In another embodiment, the bioactive hydrogel matrix is in dehydrated form and the method further comprises re-hydrating the bioactive hydrogel matrix with a re-hydrating fluid prior to administering the bioactive hydrogel matrix to the site in need of connective tissue regeneration. In dehydrated form, the bioactive hydrogel matrix can be shaped or processed into a variety of shapes and forms. For example, the dehydrated bioactive hydrogel matrix can be in a unitary piece capable of being shaped to precisely fit the site in need of connective tissue regeneration. Alternately, the dehydrated bioactive hydrogel matrix can be in particulate form. The particulate dehydrated bioactive hydrogel matrix could be mixed into a solution containing other beneficial ingredients, such as stem or progenitor cells or medicaments, combined with osteoinductive or osteoconductive materials to form a putty or paste-like material for placement into the site in need of connective tissue regeneration, or used in other preparations that would be useful in the method of the invention.

In other embodiments of the invention, it may be useful for the bioactive hydrogel matrix to have additional structure or strength in the absence of additives. Accordingly, the present invention further encompasses embodiments wherein the bioactive hydrogel matrix is in crosslinked form, the long chain carbohydrate being covalently crosslinked to the polypeptide. In such embodiments, the bioactive hydrogel matrix can be used alone in the method of the invention or may be used in conjunction with other components as described herein.

In one embodiment of the invention, the bioactive hydrogel matrix is inserted into an area of a bone in need of repair or regeneration (i.e., a bone defect). The amount of the bioactive hydrogel matrix used in the bone can vary depending upon the size of the bone defect, the form of the bioactive hydrogel matrix, and the presence or absence of additives as described herein. Typically, the total amount of the bioactive hydrogel matrix used is the amount required to fill the area of bone loss.

According to another embodiment of the present invention, the hydrogel matrix can be used for repair of soft tissue either separately or in conjunction with regeneration of nearby hard tissue, such as bone. According to this embodiment, the bioactive hydrogel matrix is administered around and/or injected into the soft tissue.

According to another embodiment of the present invention, the hydrogel matrix can be used for repair and/or regeneration of non-bone connective tissue. According to this embodiment, the bioactive hydrogel matrix is administered to an area having loss of, or damage to, connective tissue, which includes tissue arising from fibroblasts, such as tendon and ligament, or chondrocytes, such as cartilage.

According to another aspect of the present invention, there are provided various connective tissue regenerative compositions. The compositions are particularly useful in the regeneration of connective tissue or for treatment of patients having various connective tissue degenerative diseases. Accordingly, the compositions described herein are particularly useful in the methods of the invention also described herein.

In one embodiment of this aspect of the invention, the connective tissue regenerative composition comprises a three-dimensional structural framework and a bioactive hydrogel matrix at least partially contained within the three-dimensional structural framework, wherein the bioactive hydrogel matrix comprises a polypeptide and a long chain carbohydrate. The bioactive hydrogel matrix preferably further comprises one or more components selected from the group consisting of polar amino acids, polar amino acid analogues or derivatives, and divalent cation chelators, such as EDTA or salts thereof. In one particular embodiment, the three-dimensional structural framework includes a crosslinked hydrogel matrix. In another preferred embodiment, the three-dimensional structural framework includes a collage sponge.

In another embodiment, the connective tissue regenerative composition comprises at least one osteoinductive or osteoconductive material and a bioactive hydrogel matrix comprising a polypeptide and a long chain carbohydrate. The osteoinductive or osteoconductive material can be dispersed within the bioactive hydrogel matrix. In one preferred embodiment, the osteoinductive or osteoconductive material and the bioactive hydrogel matrix can be in admixture. The bioactive hydrogel matrix can be in a hydrated form or can be in a dehydrated form.

In still another embodiment of the invention, the connective tissue regenerative composition comprises stem or progenitor cells and a bioactive hydrogel matrix comprising a polypeptide and a long chain carbohydrate. Again, the bioactive hydrogel matrix can be in a hydrated form or can be in a dehydrated form.

According to another aspect of the present invention, the bioactive hydrogel matrix can be used for attaching or reattaching two or more connective tissues. In one embodiment of this aspect of the invention, the method comprises: coating at least a portion of at least one of a first and second connective tissue with a bioactive hydrogel matrix comprising a polypeptide and a long chain carbohydrate; contacting the first connective tissue to the second connective tissue at a point of attachment; and attaching the first connective tissue to the second connective tissue using sutures, staples or other appropriate means. Such a method is particularly useful for attaching connective tissue, such as tendon or ligament, to bone. The method is further useful for attaching soft connective tissue to other soft connective tissue, such as tendon to tendon or ligament to ligament.

According to another aspect of the invention, the bioactive hydrogel matrix is used in a method for treating degenerative diseases of the natural joint of a patient in need of treatment thereof. In one embodiment, the method comprises: applying to a joint affected by a degenerative disease, a bioactive hydrogel matrix comprising a polypeptide and a long chain carbohydrate. Further, optionally, the bioactive hydrogel matrix can include stem or progenitor cells. Preferentially, the administering step comprises injecting the bioactive hydrogel matrix into the affected joint. The method is particularly useful for halting progression of or reversing degenerative joint diseases, such as osteoarthritis.

The compositions and methods of the present invention are particularly useful for repairing connective tissue of the knee, such as the anterior cruciate ligament, the posterior cruciate ligament, the patellar tendon, the quadriceps tendon, and the anterior meniscofemoral ligament.

The compositions and methods of the invention are further useful for treating a patient having an artificial joint. In particular, the connective tissue regenerative compositions can be administered around the site of the artificial joint, either during placement of the artificial joint or post-surgery, to facilitate integration of the artificial joint into the surrounding tissue.

BRIEF DESCRIPTION OF THE DRAWINGS

Figure 1:
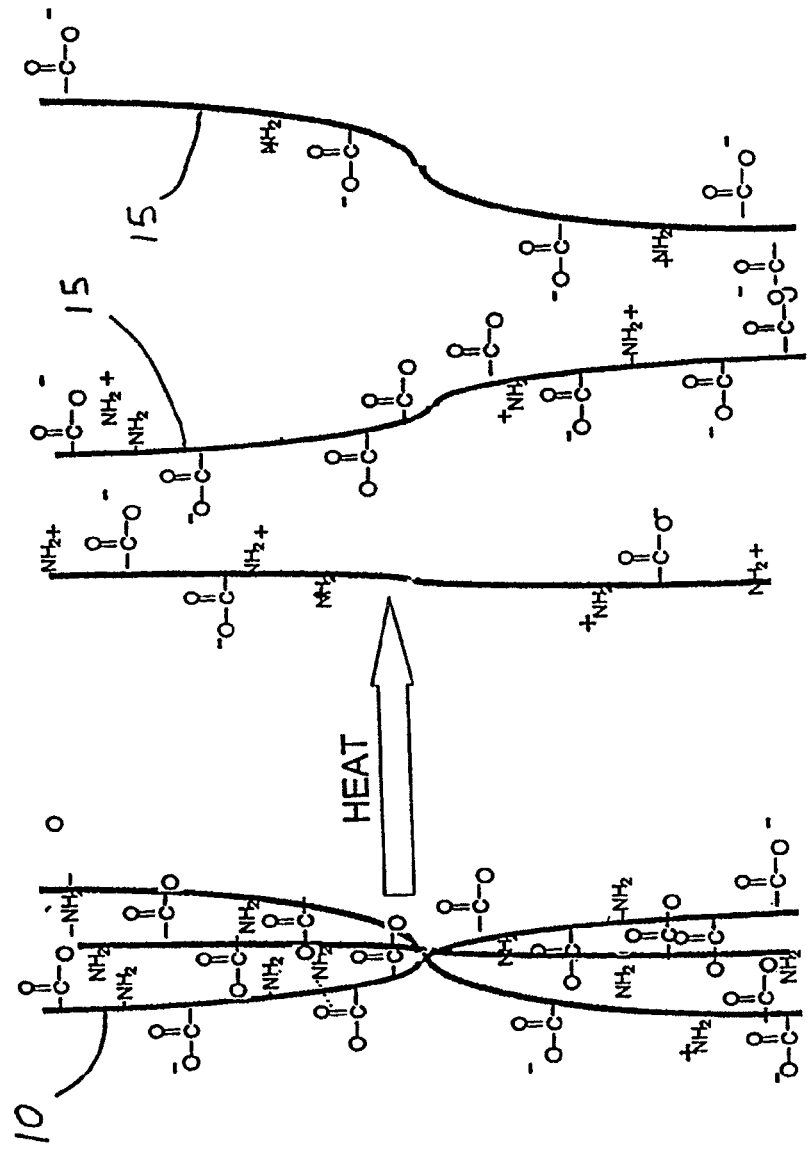
Figure 3:
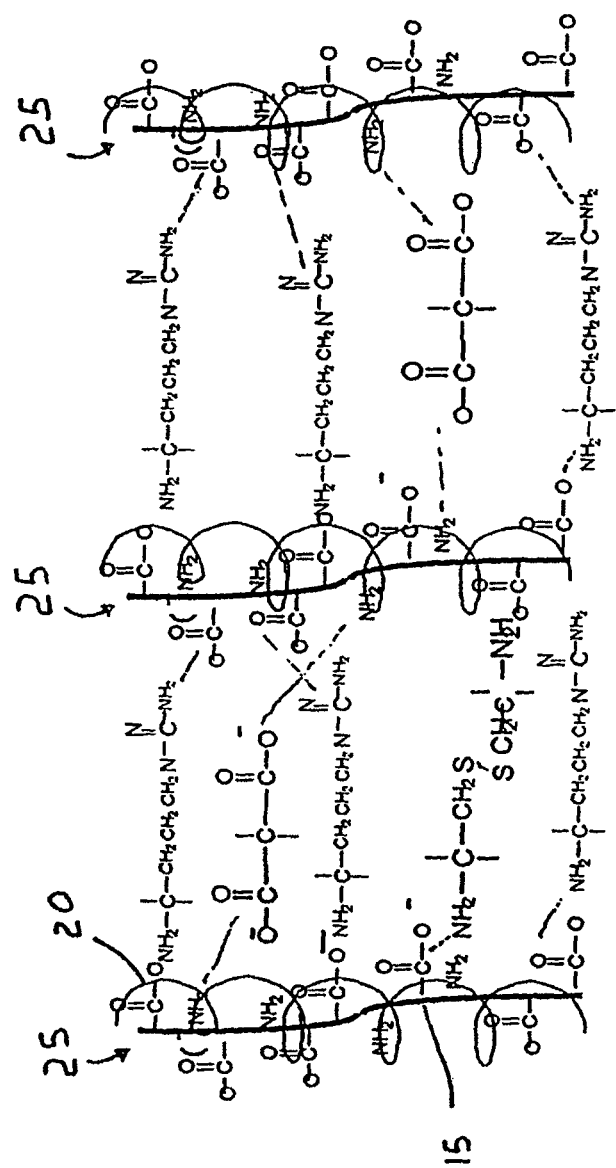
Figure 4:
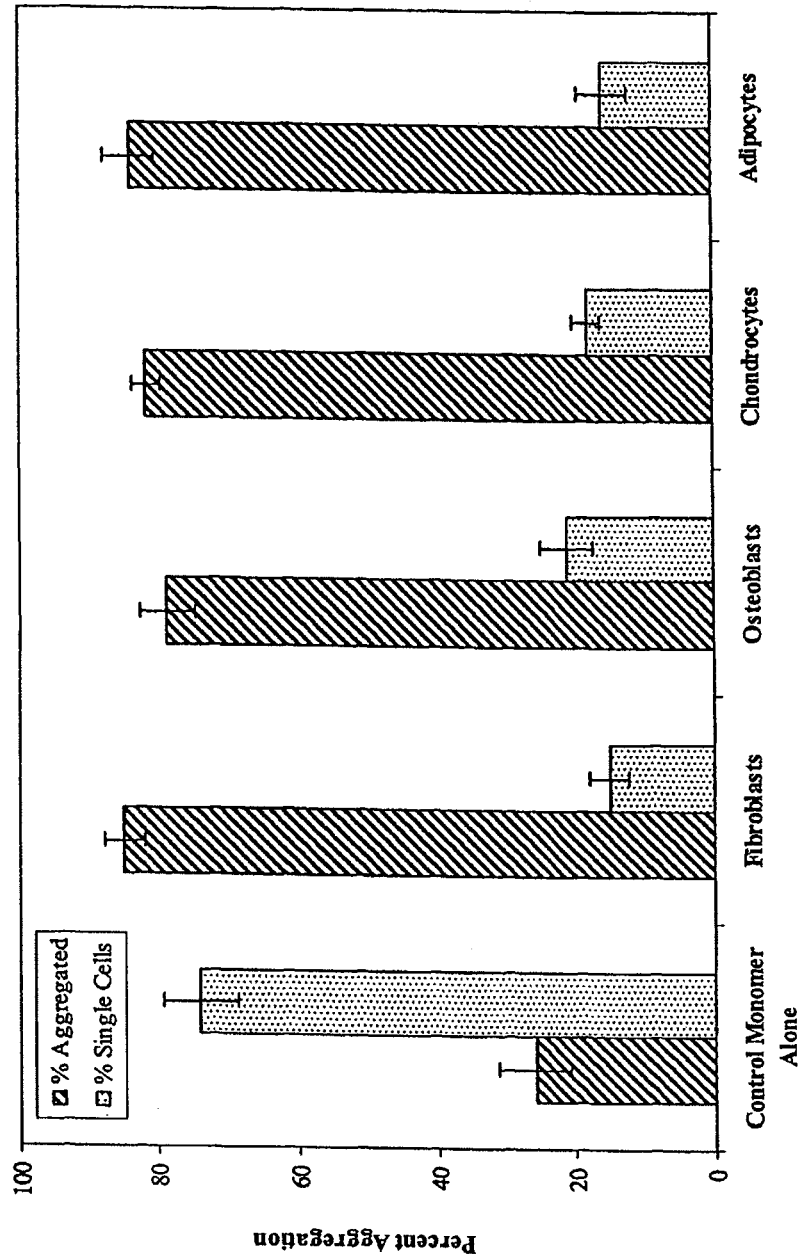
Figure 5:
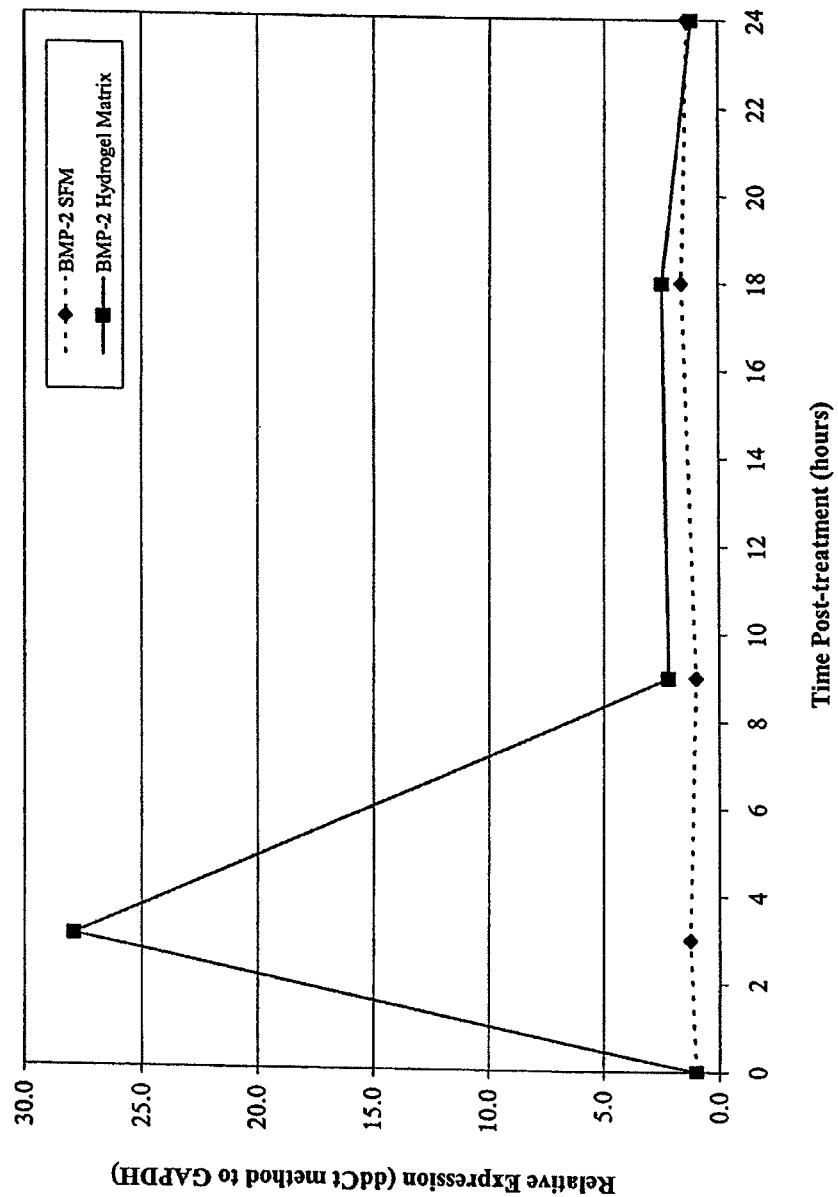
Figure 6:
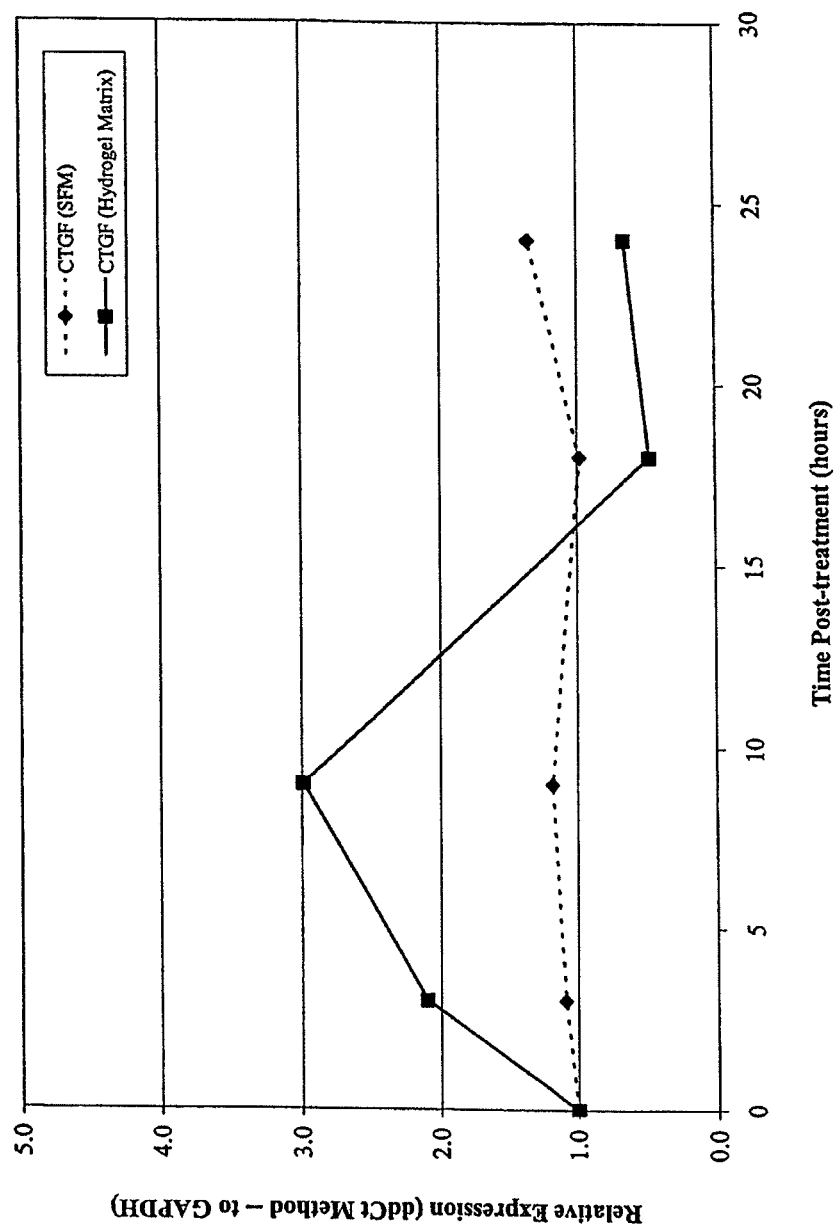
Figure 7:
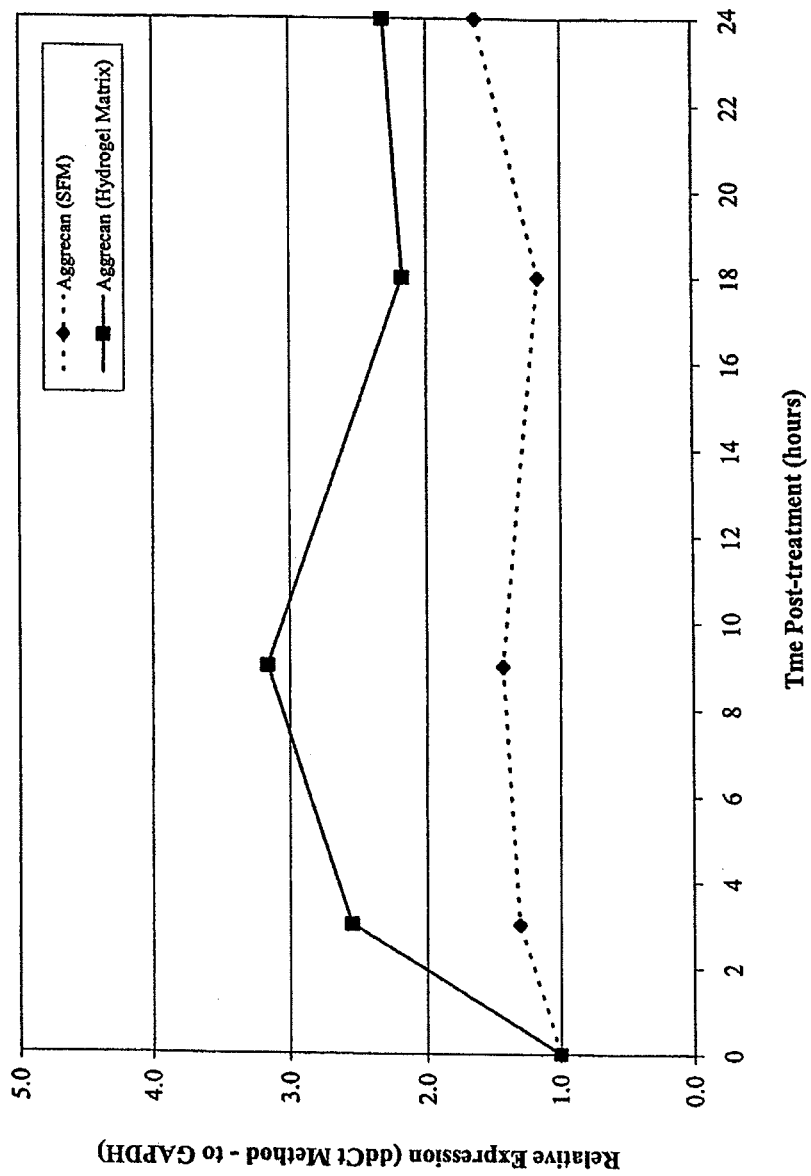
Figure 8:
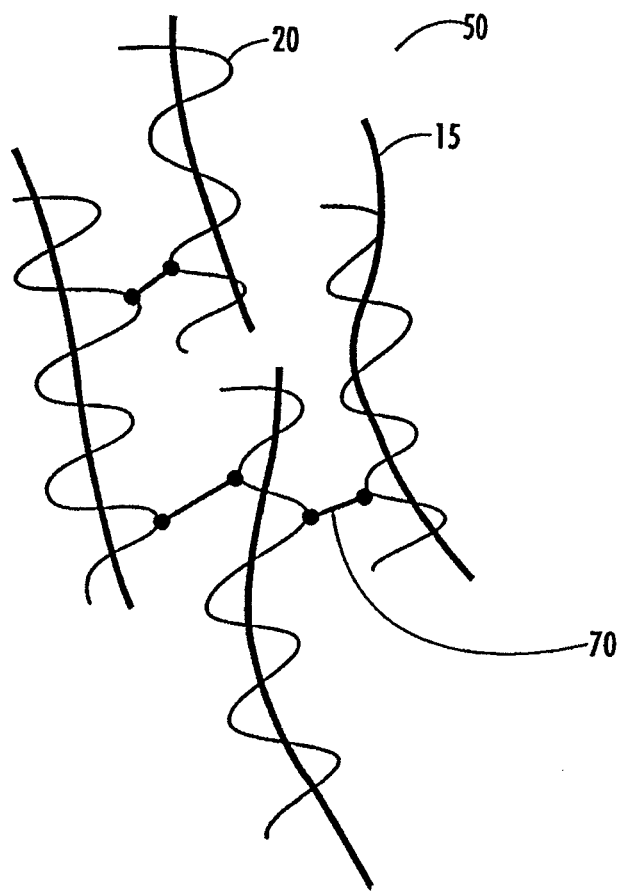
Figure 9:
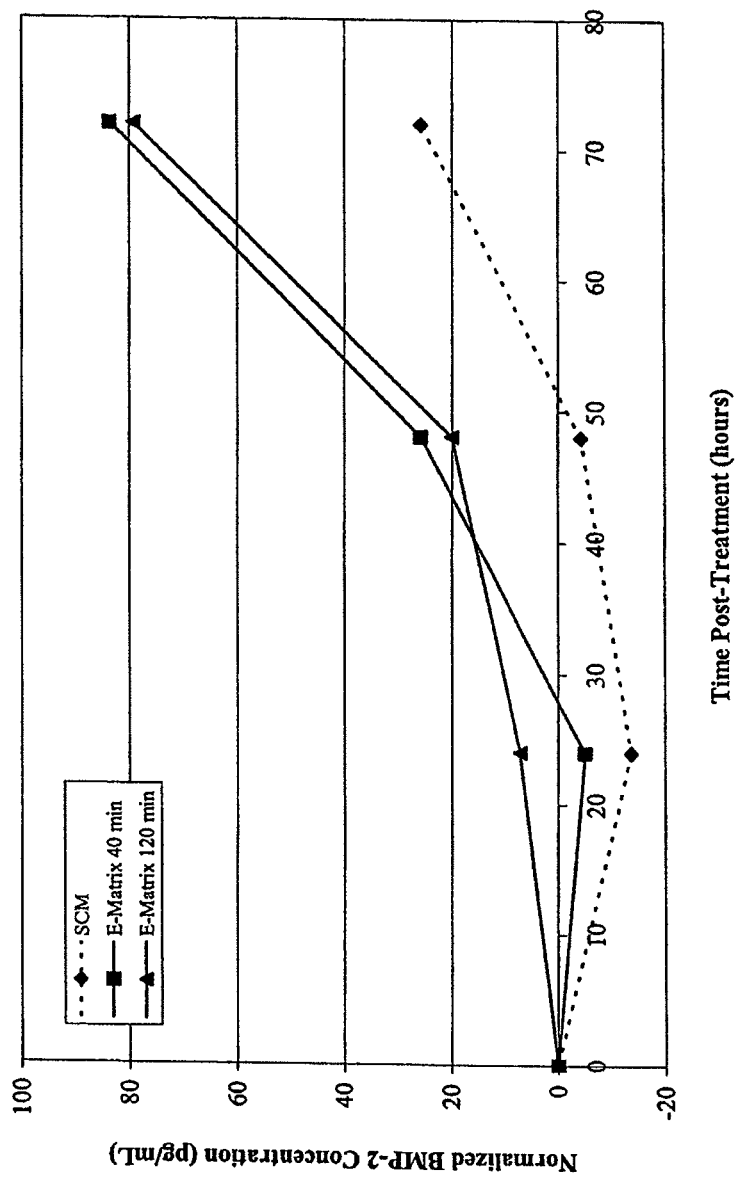
Figure 10:
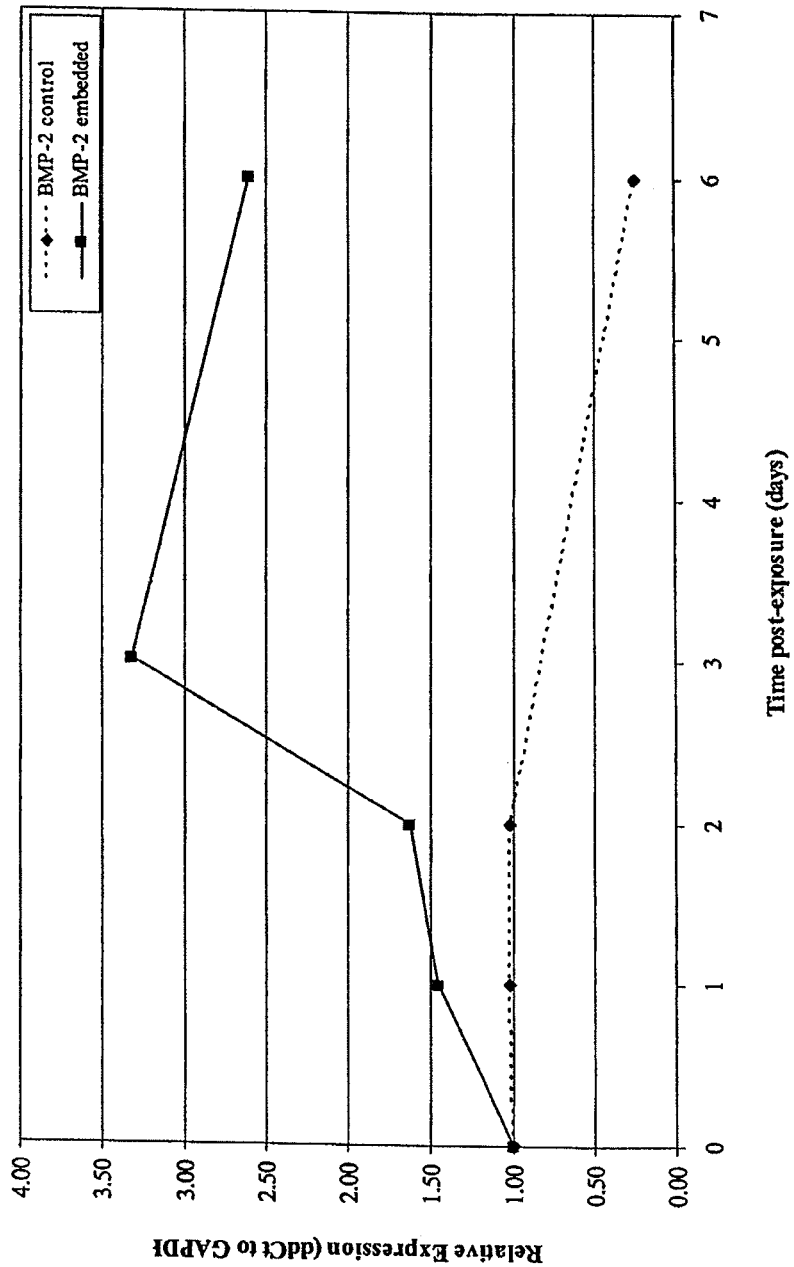

Having thus described the invention in general terms, reference will now be made to the accompanying drawings, wherein:

FIG. 1 illustrates formation of open alpha chains derived from collagen monomers;

FIGS. 2A and 2B illustrate the effect of the association of the collagen-derived alpha chains with dextran;

FIG. 3 illustrates the effect of other additives used in the bioactive hydrogel matrix of the invention;

FIG. 4 graphically illustrates cellular aggregation across various cell types in the presence of the bioactive hydrogel matrix of the present invention;

FIG. 5 illustrates the effect of the bioactive hydrogel matrix of the present invention on the expression of the BMP-2 gene as compared to expression in cells in serum free medium (SFM);

FIG. 6 illustrates the increased expression of connective tissue growth factor (CTGF) messenger RNA in chondrosarcoma cells treated with the bioactive hydrogel matrix of the invention as compared to cells in SFM;

FIG. 7 illustrates the expression of aggrecan messenger RNA in chondrosarcoma cells treated with the bioactive hydrogel matrix of the invention compared to cells in SFM;

FIG. 8 illustrates a crosslinked bioactive hydrogel matrix of the invention comprising dextran and gelatin;

FIG. 9 illustrates the effect of the bioactive hydrogel matrix of the present invention on the production of BMP-2 protein as compared to production in cells in serum containing medium (SCM); and FIG. 10 illustrates the effect of the crosslinked bioactive hydrogel matrix of the present invention on the expression of the BMP-2 gene.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The formulation of a thermoreversible hydrogel matrix providing a cell culture medium and composition for preserving cell viability is taught by U.S. Pat. No. 6,231,881, herein incorporated by reference in its entirety. Additionally, a hydrogel matrix useful in promoting vascularization is provided in U.S. Pat. No. 6,261,587, herein incorporated by reference in its entirety. The thermoreversible hydrogel matrix taught by these references is a gel at storage temperatures and molten at physiologic temperatures, and comprises a combination of a collagen-derived component, such as gelatin, a long chain carbohydrate, such as dextran, and effective amounts of other components, such as polar amino acids.

The present invention provides connective tissue regenerative compositions and methods of regenerating connective tissue at a site in need of connective tissue regeneration. The compositions and method of the invention include a bioactive hydrogel matrix generally comprising a polypeptide and a long chain carbohydrate.

A polypeptide, as used herein, is intended to encompass any tissue-derived or synthetically produced polypeptide, such as collagens or collagen-derived gelatins. Although collagen-derived gelatin is the preferred polypeptide component, other gelatin-like components characterized by a backbone comprised of sequences of amino acids having polar groups that are capable of interacting with other molecules can be used. For example, keratin, decorin, aggrecan, glycoproteins (including proteoglycans), and the like could be used to provide the polypeptide component. In one embodiment, the polypeptide component is porcine gelatin from partially hydrolyzed collagen derived from skin tissue. Polypeptides derived from other types of tissue could also be used. Examples include, but are not limited to, tissue extracts from arteries, vocal chords, pleura, trachea, bronchi, pulmonary alveolar septa, ligaments, auricular cartilage or abdominal fascia; the reticular network of the liver; the basement membrane of the kidney; or the neurilemma, arachnoid, dura mater or pia mater of the nervous system. Purified polypeptides including, but not limited to, laminin, nidogen, fibulin, and fibrillin or protein mixtures such as those described by U.S. Pat. No. 6,264,992 and U.S. Pat. No. 4,829,000, extracts from cell culture broth as described by U.S. Pat. No. 6,284,284, submucosal tissues such as those described in U.S. Pat. No. 6,264,992, or gene products such as described by U.S. Pat. No. 6,303,765 may also be used. Another example of a suitable polypeptide is a fusion protein formed by genetically engineering a known reactive species onto a protein.

The polypeptide component preferably has a molecular mass range of about 3,000 to about 3,000,000 Da, more preferably about 30,000 to about 300,000 Da, most preferably about 50,000 to about 250,000 Da. Molecular mass can be expressed as a weight average molecular mass ($M_w$) or a number average molecular mass ($M_n$). Both expressions are based upon the characterization of macromolecular solute containing solution as having an average number of molecules ($n_i$) and a molar mass for each molecule ($M_i$). Accordingly, number average molecular mass is defined by formula 1 below.

$$M_n = \frac{\sum n_i M_i}{\sum n_i} \quad (1)$$

Weight average molecular mass (also known as molecular mass average) is directly measurable using light scattering methods and is defined by formula 2 below.

$$M_w = \frac{\sum n_i M_i^2}{\sum n_i M_i} \quad (2)$$

Molecular mass can also be expressed as a Z-average molar mass ($M_z$), wherein the calculation places greater emphasis on molecules with large molar masses. Z-average molar mass is defined by formula 3 below.

$$M_z = \frac{\sum n_i M_i^3}{\sum n_i M_i^2} \quad (3)$$

Unless otherwise noted, molecular mass is expressed herein as weight average molecular mass.

In addition to molecular mass, polymer solutions can also be physically described in terms of polydispersity, which represents the broadness of the molecular mass distribution within the solution, such distribution being the range of different molecular masses of the individual polymer molecules in the solution. Polydispersity is the ratio of the number average molecular mass to the weight average molecular mass, which is defined by formula 4 below.

$$\text{Polydispersity} = \frac{M_w}{M_n} \quad (4)$$

If polydispersity is equal to 1 (i.e., $M_n$ equals $M_w$), the polymer is said to be monodisperse. A truly monodisperse polymer is one where all polymer molecules within the solution are of a single, identical molecular mass. As $M_n$ changes with $M_w$, the polydispersity changes, always being greater than 1. The polydispersity of a given polymer solution can affect the physical characteristics of the polymer, and, therefore, the interaction of the polymer with another polymer. Research has shown that in aqueous mixtures of biopolymers (including gelatin and dextran), an increase in molecular weight results in a less compatible system with a higher phase separation temperature, whereas a decrease in concentration results in a more compatible system with a lower phase separation temperature (see E. H. A. de Hoog and R. H. Tromp, On the phase separation kinetics of an aqueous biopolymer mixture in the presence of gelation: the effect of the quench depth and the effect of the molar mass, Colloids and Surfaces A: Physicochemical and Engineering Aspects, 213 (2-3), Pages 221-234). Preferably, the polypeptide used according to the present invention has a polydispersity close to 1. In one preferred embodiment, the polypeptide has a polydispersity of 1 to about 4, more preferably, about 1 to about 3, most preferably about 1.1 to about 2.4.

The polypeptide used in the bioactive hydrogel matrix of the invention is preferably a gelatin, such as collagen derived gelatin.

Collagen is a major protein component of the extracellular matrix of animals. Early in fetal development, a more open form of collagen (compared to tightly bound mature collagen) is associated with large carbohydrate molecules, and serves as the predominant tissue scaffolding. It is believed that attachment of differentiated or incompletely differentiated cells of mesenchymal origin to this polar, proteoglycan-like, collagen scaffolding results in a specific host tissue response. This response is to guide the differentiation of mesenchymal tissue.

Collagen is assembled into a complex fibrillar organization. The fibrils are assembled into bundles that form the fibers. The fibrils are made of five microfibrils placed in a staggered arrangement. Each microfibril is a collection of collagen rods. Each collagen rod is a right-handed triple-helix, each strand being itself a left-handed helix. Collagen fibrils are strengthened by covalent intra- and intermolecular cross-links which make the tissues of mature animals insoluble in cold water. When suitable treatments are used, collagen rods are extracted and solubilized where they keep their conformation as triple-helices. This is denatured collagen and differs from the native form of collagen, but has not undergone sufficient thermal or chemical treatment to break the intramolecular stabilizing covalent bonds found in collagen. When collagen solutions are extensively heated, or when the native collagen containing tissues are subjected to chemical and thermal treatments, the hydrogen and covalent bonds that stabilize the collagen helices are broken, and the molecules adopt a disordered conformation. By breaking these hydrogen bonds, the polar amine and carboxylic acid groups are now available for binding to polar groups from other sources or themselves. This material is gelatin and is water-soluble at 40-45° C.

As noted above, gelatin is a form of denatured collagen, and is obtained by the partial hydrolysis of collagen derived from the skin, white connective tissue, or bones of animals. Gelatin may be derived from an acid-treated precursor or an alkali-treated precursor. Gelatin derived from an acid-treated precursor is known as Type A, and gelatin derived from an alkali-treated precursor is known as Type B. The macromolecular structural changes associated with collagen degradation are basically the same for chemical and partial thermal hydrolysis. In the case of thermal and acid-catalyzed degradation, hydrolytic cleavage predominates within individual collagen chains. In alkaline hydrolysis, cleavage of inter- and intramolecular cross-links predominates.

Preferably, the gelatin used in the present invention is skin-derived gelatin or bone derived gelatin. In one preferred embodiment, the gelatin has a molecular mass of about 80,000 Da to about 200,000 Da. Further, it is preferred that the gelatin have a polydispersity of 1 to about 3. In one preferred embodiment, the gelatin has a polydispersity of about 1.1 to about 2.4.

The polypeptide, such as gelatin, is preferentially present at a concentration of about 0.01 to about 40 mM, preferably about 0.05 to about 30 mM, most preferably about 0.25 to about 5 mM. Advantageously, the gelatin concentration is approximately 0.75 mM. The above concentrations provide a non-flowable phase at storage temperature (below about 33° C.) and a flowable phase at treatment temperature (about 35 to about 40° C.).

The bioactive hydrogel matrix of the present invention also comprises a long chain carbohydrate. The phrase long chain carbohydrate is generally intended to encompass any polysaccharide or sulfated polysaccharide consisting of more than about 10 monosaccharide residues joined to each other by glycosidic linkages. The phrase is also intended to encompass other long chain carbohydrates, including heterosaccharides, and specific classes of carbohydrates, such as starches, sugars, celluloses, and gums. The long chain carbohydrate may consist of the same monosaccharide residues, or various monosaccharide residues or derivatives of monosaccharide residues. Dextran, a preferred polysaccharide, solely comprises glucose residues.

Any polysaccharide, including glycosaminoglycans (GAGs) or glucosaminoglycans, with suitable viscosity, molecular mass and other desirable properties may be utilized in the present invention. By glycosaminoglycan is intended any glycan (i.e., polysaccharide) comprising an unbranched polysaccharide chain with a repeating disaccharide unit, one of which is always an amino sugar. These compounds are a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glucosaminoglycan is intended any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

The long chain carbohydrate preferably has a molecular mass of about 2,000 to about 8,000,000 Da, more preferably about 20,000 to about 1,000,000 Da, most preferably about 200,000 to about 800,000 Da. In one embodiment, the long chain carbohydrate has a molecular mass of approximately 500,000 Da.

Preferably, the long chain carbohydrate used according to the present invention has a polydispersity close to 1. In one preferred embodiment, the polypeptide has a polydispersity of 1 to about 3, more preferably, about 1.1 to about 2.4.

As previously noted, one preferred long chain carbohydrate for use in the present invention is dextran. Dextran typically comprises linear chains of $\alpha(1\rightarrow 6)$-linked D-glucose residues, often with $\alpha(1\rightarrow 2)$- or $\alpha(1\rightarrow 3)$-branches. Native dextran, produced by a number of species of bacteria of the family Lactobacilliaceae, is a polydisperse mixture of components. Dextrans have been widely used as plasma substitutes and blood extenders, are considered fully biocompatible, and are metabolizable. Dextrans are available in a wide range of average molecular masses, varying from about 4,000 to about 40,000,000 Da. Preferably, the dextran used in the invention has a molecular mass of about 200,000 to about 800,000 Da, most preferably about 300,000 to about 600,000 Da. In one preferred embodiment, the dextran has a molecular mass of approximately 500,000 Da. Dextrans have varying rates of resorption in vivo from about two to about 20 days depending on their molecular mass.

The long chain carbohydrate, such as dextran, is preferentially present at a concentration of about 0.01 to about 10 mM, preferably about 0.01 to about 1 mM, most preferably about 0.01 to about 0.5 mM. In one embodiment, dextran is present at a concentration of about 0.1 mM.

While native dextran is generally used in the present invention, the use of dextran derivatives, such as dextran sulfate and dextran phosphate is also within the scope of the invention. In one embodiment, the derivatives are free radical polymerizable, preferably photopolymerizable derivatives, such as acrylates. According to this embodiment, the composition can be injected as a viscous liquid and polymerized in situ to form a solid material. The dextran can also be selected to degrade at a rate which approximates ingrowth of new bone or tissue. Those compositions that include free radical polymerizable groups may also include polymerization initiators, such as photoinitiators, such as benzoin ethers, and thermally activatable initiators, such as azobisisobutyronitrile (AIBN) and di-t-butyl ether. Free radical polymerization initiators, and conditions for carrying out free radical polymerizations, are well known to those of skill in the art, and any of such methods are encompassed by the present invention.

In a preferred embodiment, gelatin and dextran are components of the bioactive hydrogel matrix of the present invention. For ease of describing the invention, the terms "gelatin" and "dextran" are used throughout with the understanding that various alternatives as described above, such as other polypeptides and other long chain carbohydrates readily envisioned by those skilled in the art, are contemplated by the present invention.

Although not bound by any particular theory, the present invention is intended to provide a matrix scaffolding designed to maximize the polar amino acid hydrogen bonding sites found in alpha chains derived from collagen. These alpha chains, or gelatin, are preferably derived from pig gelatin, and stabilized by 500,000 Da molecular mass dextran, or other long chain carbohydrates, added while the alpha chains are heated. The positively charged polar groups of the collagen-derived alpha chains are then able to associate with the negatively charged —OH groups of the repeating glucose units found in the dextran. The gelatin and the dextran form a proteoglycan-type structure. FIGS. 1-3 illustrate the interaction between the various components of the preferred embodiment of the matrix of the invention and interaction between the matrix and the tissue of a patient.

FIG. 1 illustrates the creation of polar alpha chains 15 from tropocollagen 10 derived from mature collagen. Heating tropocollagen 10 disrupts the hydrogen bonds that tightly contain the triple stranded monomers in mature collagen. By breaking these hydrogen bonds, the polar amine and carboxylic acid groups are now available for binding to polar groups from other sources or themselves.

FIGS. 2A-2B illustrate stabilization of the matrix monomeric scaffolding by the introduction of a long chain carbohydrate 20, such as dextran. As shown in FIG. 2B, without the long chain carbohydrate 20, the alpha chain 15 will form hydrogen bonds between the amino and carboxylic acid groups within the linear portion of the monomer and fold upon itself, thus limiting available sites for cellular attachment. As depicted in FIG. 2A, the long chain carbohydrate 20 serves to hold the alpha chain 15 open by interfering with this folding process.

In addition to the polypeptide and long chain carbohydrate, the bioactive hydrogel matrix can further comprise one or more components useful for enhancing the bioadhesiveness of the hydrogel matrix. Examples of such components include polar amino acids, polar amino acid analogues or derivatives, divalent cation chelators, and combinations thereof. In one preferred embodiment, all of the bioactive hydrogel matrix ingredients are provided in admixture.

The bioactive hydrogel matrix preferably includes one or more polar amino acids in an effective amount to increase the rigidity of the hydrogel matrix and allow direct administration of the hydrogel matrix, such as through injection, to a site in need of connective tissue regeneration. As used herein, polar amino acids are commonly defined and intended to include tyrosine, cysteine, serine, threonine, asparagine, glutamine, asparatic acid, glutamic acid, arginine, lysine, and histidine. Peferentially, the amino acids are selected from the group consisting of cysteine, arginine, lysine, histidine, glutamic acid, aspartic acid. When polar amino acids are present in the bioactive hydrogel matrix, the polar amino acids are preferentially present in a concentration of about 3 to about 150 mM, preferably about 10 to about 65 mM, and more preferably about 15 to about 40 mM.

Advantageously, the added polar amino acids comprise L-glutamic acid, L-lysine, and L-arginine. The final concentration of L-glutamic acid is generally about 2 to about 60 mM, preferably about 5 to about 40 mM, most preferably about 10 to about 30 mM. In one embodiment, the concentration of L-glutamic acid is about 20 mM. The final concentration of L-lysine is generally about 0.5 to about 30 mM, preferably about 1 to about 15 mM, most preferably about 1 to about 10 mM. In one embodiment, the concentration of L-lysine is about 5.0 mM. The final concentration of L-arginine is generally about 1 to about 40 mM, preferably about 1 to about 30 mM, most preferably about 5 to about 20 mM. In one embodiment, the final concentration of arginine is about 15 mM.

By amino acid is intended all naturally occurring alpha amino acids in both their D and L stereoisomeric forms, and their analogues and derivatives. An analog is defined as a substitution of an atom or functional group in the amino acid with a different atom or functional group that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine. As previously noted, the bioactive hydrogel matrix of the invention can include one or more polar amino acid analogues or derivatives.

Amino acids used in the bioactive hydrogel matrix of the present invention can also be present as dipeptides, which are particular beneficial for delivery of amino acids having decreased water solubility, such as L-glutamine. Accordingly, amino acids added to the hydrogel matrix can include dipeptides, such as L-alanyl-L-glutamine. When present in the hydrogel matrix, the concentration range for L-alanyl-L-glutamine is preferably about 0.001 to about 1 mM, more preferably about 0.005 to about 0.5 mM, most preferably about 0.008 to about 0.1 mM. In one particular embodiment, the final concentration of L-alanyl-L-glutamine is about 0.01 mM.

The added amino acids can also include L-cysteine, which is advantageous in many regards. Cysteine is useful for providing disulfide bridges, further adding support and structure to the bioactive hydrogel matrix and increasing its resistance to force. The final concentration of L-cysteine is generally about 5 to about 5000 µM, preferably about 10 to about 1000 µM, most preferably about 100 to about 1000 µM. In one embodiment, the final concentration of cysteine is about 700 µM. L-cysteine also acts as a nitric oxide scavenger or inhibitor. Nitric oxide inhibitors include any composition or agent that inhibits the production of nitric oxide or scavenges or removes existing nitric oxide. Nitric oxide, a pleiotropic mediator of inflammation, is a soluble gas produced by endothelial cells, macrophages, and specific neurons in the brain, and is active in inducing an inflammatory response. Nitric oxide and its metabolites are known to cause cellular death from nuclear destruction and related injuries.

Accordingly, the bioactive hydrogel matrix can optionally include one or more additional nitric oxide inhibitors, such as aminoguanidine, N-monomethyl-L-arginine, N-nitro-L-arginine, cysteine, heparin, and mixtures thereof. When present in the hydrogel matrix, the final concentration of nitric oxide inhibitors is generally about 5 to about 500 µM, preferably about 10 to about 100 µM, most preferably about 15 to about 25 µM. In one embodiment, the final concentration is about 20 µM.

Advantageously, intact collagen can be optionally added to the bioactive hydrogel matrix to provide an additional binding network and provide additional support to the matrix. The final concentration of the intact collagen present in the hydrogel matrix is from about 0 to about 5 mM, preferably about 0 to about 2 mM, most preferably about 0.05 to about 0.5 mM.

Additionally, the bioactive hydrogel matrix may optionally include one or more divalent cation chelators, which increase the rigidity of the matrix by forming coordinated complexes with any divalent metal ions present. The formation of such complexes leads to the increased rigidity of the matrix by removing the inhibition of hydrogen bonding between —$NH_2$ and —COOH caused by the presence of the divalent metal ions. A preferred example of a divalent cation chelator that is useful in the present invention is ethylenediaminetetraacetic acid (EDTA) or a salt thereof. The concentration range for the divalent cation chelator, such as EDTA, is generally about 0.01 to about 10 mM, preferably 1 to about 8 mM, most preferably about 2 to about 6 mM. In a one embodiment, EDTA is present at a concentration of about 4 mM.

EDTA is also an example of another group of compounds useful as additives for the bioactive hydrogel matrix, superoxide inhibitors. Superoxide is a highly toxic reactive oxygen species, whose formation is catalyzed by divalent transition metals, such as iron, manganese, cobalt, and sometimes calcium. Highly reactive oxygen species such as superoxide ($O_2^-$) can be further converted to the highly toxic hydroxyl radical ($OH^-$) in the presence of iron. By chelating these metal catalysts, EDTA serves as an antioxidant. Accordingly, the bioactive hydrogel matrix can include one or more superoxide inhibitor.

Optionally, trace mineral nutrients and salts thereof, such as zinc sulfate, can be added to the bioactive hydrogel matrix. Zinc has beneficial wound healing effects that are particularly useful in the present invention. When present in the hydrogel matrix, the concentration range for zinc is generally about 0.005 mM to about 3 mM, preferably about 0.01 to about 2 mM, most preferably about 0.02 to about 1 mM. In one particular embodiment, the final concentration of zinc is about 0.03 mM.

The bioactive hydrogel matrix is preferably based upon a physiologically compatible buffer, one embodiment being Medium 199, a common nutrient solution used for in vitro culture of various mammalian cell types (available commercially from Sigma Chemical Company, St. Louis, Mo.). The buffer can be further supplemented with additives and additional amounts of some medium components, such as supplemental amounts of polar amino acids as described above.

The bioactive hydrogel matrix can also be formulated in other buffered solutions, including buffered solutions regarded as simplified in relation to Medium 199. For example, a phosphate buffer formulated to yield physiological osmotic pressures after hydrogel matrix compounding can be prepared using 1.80 mM $KH_2PO_4$ and 63 mM $Na_2HPO_4$.

The bioactive hydrogel matrix of the present invention is particularly useful for repairing and regenerating connective tissue because of the open structure of the hydrogel matrix and the inherent ability of the hydrogel matrix to interact with physiological material. FIG. 3 illustrates the effect of polar amino acids and/or L-cysteine added to stabilize the monomer/carbohydrate units 25 by linking the exposed monomer polar sites to, for example, arginine's amine groups or glutamic acid's carboxylic acid groups. Furthermore, disulfide linkages can be formed between L-cysteine molecules (thereby forming cystine), which in turn forms hydrogen bonds to the monomeric alpha chains 15. The stability imparted by the polar amino acids, polar amino acid analogues and derivatives, and intact collagen is particularly advantageous for maintaining the open structure of the gelatin and keeping the active sites available for therapeutic benefit.

The hydrogen bonds formed between these additional amino acids and monomer/carbohydrate units 25 are broken when the matrix is liquefied upon heating, and the polar groups are freed to attach the monomer/dextran units to exposed patient tissue surfaces. In preferred embodiments, EDTA or a salt thereof is also present to chelate divalent cations and thereby prevent divalent cations from being preferentially attracted to the exposed polar groups of the monomer/carbohydrate units 25 to the exclusion of the polar amino acids.

Normally, the tearing of tissue secondary to trauma stimulates production and release of nitric oxide, initiating recruitment of immune and inflammatory cells that phagocytise or release chemicals to destroy foreign substances. By providing local and temporal inhibition of nitric oxide and superoxide release and production, nitric oxide inhibitors, such as aminoguanidine and cysteine, and superoxide inhibitors, such as EDTA, allow the collagen derived alpha chain/dextran units 25 to bind and become integrated on the exposed tissue surface. The alpha chain/dextran units 25 then serve as the scaffolding on which formerly differentiated host cells de-differentiate into "mesenchymoid" morphology. This de-differentiation process is followed by integration of these incompletely differentiated cells into host tissue. These mesenchymoid cells are then able to promote areas of their genome that leads to differentiation into cell types required for tissue healing and regeneration.

By providing a proteoglycan-like scaffolding similar to that found in the early stages of fetal development, and using structural stabilizers that serve a secondary purpose in enhancing host response to the scaffolding upon exposure to host tissues, the matrix serves as a biocompatible device capable of increasing vascularization and promoting wound healing and local tissue regeneration, even in the case of large areas of bone loss. Because the matrix promotes tissue-specific regeneration, as occurs during embryogenesis and fetogenesis where similar types of scaffolding are present, it has now been discovered that the matrix of the invention can be used to successfully treat bone injuries that are typically non-responsive to conventional treatments, such as long segmental diaphyseal bone loss, cavitation, and simple fractures in patients having abnormally low ability to regenerate bone tissue. Furthermore, it has been discovered that the bioactive hydrogel matrix of the present invention can be used to successfully treat additional types of injuries often known to be difficult to treat or slow to heal, such as injuries to non-bone connective tissues, such as tendon, ligament, and cartilage.

In vitro testing has shown that the bioactive hydrogel matrix of the invention exhibits a remarkable ability to bind to and hence promote cell aggregation across multiple cell types. Treatment of cultured osteoblasts (human osteosarcoma cell line SAOS-2) with the bioactive hydrogel matrix resulted in approximately 80% cellular aggregation. In one comparative study, cells were treated with the bioactive hydrogel matrix of the invention, and cells (control) were treated with gelatin alone. Cell types tested were fibroblasts, osteoblasts, chondrocytes, and adipocytes. The cells were stained with trypan blue and visually inspected. The cells treated with the bioactive hydrogel matrix were evident as large clumps (i.e., aggregates), while the control cells (those treated with gelatin alone) were evident as single cells and not aggregated. This illustrates how the intact bioactive hydrogel matrix binds to and aggregates cells important in wound healing, bone repair, and non-bone connective tissue repair. This binding and subsequent interaction does not occur when only gelatin is present. Furthermore, previous similar studies with fibroblasts indicated the binding and aggregation also did not occur after treatment with dextran alone.

FIG. 4 provides quantification of the aggregation of the cells in the study described above. As shown in FIG. 4, after treatment with the bioactive hydrogel matrix of the invention, all four cell types demonstrated approximately 80% aggregation. Comparatively, the cells treated with gelatin alone demonstrated less than 30% aggregation. The binding of the bioactive hydrogel matrix to cells as evidenced by the aggregation is believed to be the first key step in the action of the bioactive hydrogel matrix on cellular activity. The aggregation is a result of the cells interacting with the open polar co-polymer structure of the bioactive hydrogel matrix.

The bioactive hydrogel matrix of the invention also exhibits additional action necessary for bone regeneration. In one study, treatment of cultured osteoblasts with the bioactive hydrogel matrix of the invention resulted in a greater than 20-fold increase in bone morphogenetic protein-2 (BMP-2) messenger RNA. BMP-2 is a member of the transforming growth factor (TGF) beta superfamily of proteins and a key regulator of osteoblast differentiation. BMP is known to stimulate wound healing and includes various bone morphogenetic proteins in addition to BMP-2. This alteration and increase of gene activity is indicative of the ability of the matrix to produce healing of bone fractures. This activity of the bioactive hydrogel matrix in stimulating BMP-2 production is illustrated in FIG. 5, which demonstrates an acute and dramatic increase in BMP-2 gene expression after a 40 minute treatment with the bioactive hydrogel matrix as compared to a control.

The useful activity of the bioactive hydrogel matrix is further demonstrated in FIGS. 6 and 7, which illustrate the effects of treatment of cultured chondrocytes (cells leading to the production of tendon, ligament, and cartilage) with the bioactive hydrogel matrix of the invention in causing a greater than 3-fold increase in Connective Tissue Growth Factor (CTGF) and aggrecan gene expression. CTGF is a profibrotic protein induced by TGF beta and is a key regulator of chondrocyte proliferation and differentiation. It is an early marker of chondrogenesis expressed at the highest levels in vivo during chondrocyte growth. Aggrecan is a major cartilage extracellular matrix (ECM) component and a marker for the chondrocyte phenotype. FIG. 6 again illustrates an acute and marked increase in CTGF gene expression in the presence of the bioactive hydrogel matrix. FIG. 7 illustrates a similar increase in aggrecan gene expression and also illustrates a more prolonged effect of such increase.

In addition to being in its usual, hydrated form (as generally described above), the bioactive hydrogel matrix of the present invention can further be in a dehydrated form. This is a particularly advantageous form of the bioactive hydrogel matrix increasing the practical usefulness of the hydrogel matrix, providing for ease of storage and transportation, and preserving the shelf-life of the hydrogel matrix and compositions made using the hydrogel matrix. Any method generally known in the art for dehydrating materials normally in a hydrated state would be useful according to the present invention, so long as it is not detrimental to the connective tissue regenerative properties of the hydrogel matrix as described herein. For example, one preferred method of dehydrating the bioactive hydrogel matrix is freeze drying. Other methods of preparing dehydrated biopolymers, such as spray-drying or speed-vac, can also be used and are known to those skilled in the art.

Freeze drying generally comprises the removal of water or other solvent from a frozen product through sublimation, which is the direct transition of a material (e.g., water) from a solid state to a gaseous state without passing through the liquid phase. Freeze drying allows for the preparation of a stable product being readily re-hydratable, easy to use, and aesthetic in appearance. The freeze drying process consists of three stages: 1) pre-freezing, 2) primary drying, and 3) secondary drying.

Since freeze drying involves a phase change from solid to gaseous, material for freeze drying must first be adequately pre-frozen. The pre-freezing method and the final frozen product temperature can both affect the ability to successfully freeze dry the material. Rapid cooling forms small ice crystals. While small crystals are useful in preserving structure, they result in a product that is more difficult to freeze dry. Slower cooling results in larger ice crystals and produces less restrictive channels in the matrix during the drying process. Pre-freezing to temperatures below the eutectic temperature, or glass transition temperature, is necessary for complete drying of hydrogels. Inadequate freezing may produce small pockets of unfrozen material remaining in the product which may expand and compromise the structural stability of the freeze dried product.

After pre-freezing the product, conditions must be established in which ice (i.e., frozen solvent) can be removed from the frozen product via sublimation, resulting in a dry, structurally intact product. This requires careful control of the two parameters, temperature and pressure, involved in the freeze drying system. It is important that the temperature at which a product is freeze dried is balanced between the temperature that maintains the frozen integrity of the product and the temperature that maximizes the vapor pressure of the solvent.

After primary freeze drying is complete, and all ice has sublimed, bound moisture is still present in the product. The product appears dry, but the residual moisture content may be as high as 7-8%. Continued drying is necessary at a warmer temperature to reduce the residual moisture content to optimum values. This process is called isothermal desorption, as the bound water is desorbed from the product. Secondary drying is normally continued at a product temperature higher than ambient but compatible with the sensitivity of the product. All other conditions, such as pressure and collector temperature, remain the same. Because the process is desorptive, the vacuum should be as low as possible (no elevated pressure) and the collector temperature as cold as can be attained. Secondary drying is usually carried out for approximately ⅓ to ½ the time required for primary drying.

One example of equipment useful in preparing freeze dried hydrogels is the FreeZone 12 Liter Freeze Dry System with Stoppering Tray Dryer (Labconco Kansas City, Mo.). With such system, tubes with porous caps containing hydrogels are frozen to −30° C. at a cooling rate of 0.05° C./min using the cooling shelf unit of the freeze dryer and are held at −30° C. for 12 hours. A vacuum is applied to the frozen hydrogel at −30° C. for 24 hours before the temperature is incrementally increased to −10° C. at a rate of 0.25° C./minute. The hydrogel is held under vacuum at −10° C. for at least 12 hours before the temperature is further increased to 20° C. at a rate of 0.05° C./minute.

The dehydrated bioactive hydrogel matrix can comprise the bioactive hydrogel matrix in any of the embodiments described herein. Furthermore, the bioactive hydrogel matrix can be used in preparing any of the connective tissue regenerative compositions described herein prior to being dehydrated. Therefore, the present invention also encompasses dehydrated connective tissue regenerative compositions.

In one embodiment of the invention, the bioactive hydrogel matrix can be prepared as described herein and then dehydrated to form a single mass. The single mass can then be customized for specific uses. For example, the dehydrated hydrogel matrix could be sliced into wafer-like slices of varying dimensions. The dehydrated hydrogel matrix could also be ground to a particulate form. The dehydrated hydrogel matrix could also be cut to various shapes and dimensions for specified uses, such as preformed plugs for use in bone cavitation. Also, advantageously, the dehydrated bioactive hydrogel matrix could be formed to a standardized shape and size and packaged for various uses. The pre-packaged dehydrated bioactive hydrogel matrix could then be customized to a desired shape and size at the time of use. In a further embodiment, the dehydrated hydrogel matrix can be shaped around a central mandrel to form porous tubes useful for tissue regenerative guidance conduits. These can be wrapped around specific sites which may require or benefit from guided tissue regeneration. Dehydrated hydrogels can also be partially rehydrated to form putties and pastes appropriate for filling bony voids caused by surgery or trauma.

The dehydrated hydrogel matrix, when re-hydrated, retains is connective tissue regenerative properties as described herein and can be used according to the methods of the invention as effectively as a freshly prepared bioactive hydrogel matrix of the invention. The re-hydration of the hydrogel matrix can be performed according to various methods, all of which are encompassed by the invention. In one embodiment, the dehydrated bioactive hydrogel matrix is re-hydrated immediately prior to use, such as by contacting with water or a physiologically compatible buffer solution, such as Medium 199. In another embodiment, the dehydrated bioactive hydrogel matrix could be placed in the site in need of connective tissue regeneration and then contacted with re-hydrating fluids, such as water or a physiologically compatible buffer solution. In still another embodiment, the dehydrated hydrogel matrix could be placed in the site in need of connective tissue regeneration and then re-hydrated through contact with natural body fluids.

It is, of course, understood that any of the above embodiments described in relation to the dehydrated hydrogel matrix are also intended to encompass similar or identical embodiments using the connective tissue regenerative compositions of the present invention comprising the bioactive hydrogel matrix.

While the bioactive hydrogel matrix of the present invention is useful in multiple types of tissue repair, it is particularly advantageous in areas where tissue repair or regeneration is especially difficult. As described previously, such is often the case with bone regeneration and repair of non-bone connective tissue. Connective tissue is a generalized term for mesodermally derived tissue that may be more or less specialized. Many types of tissue can fall under the term, such as bone, cartilage, dura mater, tendon, and ligament. The term can also be used for less specialized tissue that is rich in components such as collagen and proteoglycans, and that surrounds other more highly ordered tissues and organs.

The bioactive hydrogel matrix is especially useful in the regeneration of bone, particularly in situations where bone repair does not occur or where more rapid healing of a bone defect would be beneficial to a patient. In situations where there is bone loss over of relatively large area of the bone, the bioactive hydrogel matrix can be inserted into the area of the bone loss and allowed to remain in place to facilitate healing of the wound and regeneration of bone in the area of the loss. The matrix provides multiple regenerative functions as described above. The matrix interacts with osteocytes leading to more rapid formation of bone tissue. The matrix also promotes osteoblast gene expression as demonstrated by the increased production of BMP-2. The presence of the matrix in the wound site also inhibits ingrowth of non-bone tissue into the wound inhibiting the formation of new bone tissue. The presence of the matrix also promotes vascularization, which is necessary for the rapid growth of new bone tissue in providing nutrients, growth factors, oxygen, and other components necessary to bone regeneration.

Closely related to the ability of the matrix to promote regeneration of bone is the function of the matrix in relation to stem or progenitor cells. This is an important aspect of the ability of the matrix to support tissue regeneration for multiple reasons. First, stem cells are found in bone marrow, and these adult stem cells can be induced to differentiate into bone tissue or other types of connective tissue, including cartilage, and important adjacent tissues, such as neurons and skeletal muscle. Further, progenitor cells, which are precursors giving rise to cells of a particular cell type, are also useful for inducing bone tissue growth, or other connective tissue growth, where applicable. Thus, interacting with those cells in the areas surrounding bone injury, for example, could stimulate stem or progenitor cells in the injured area to differentiate into bone cells, further hastening the regeneration of the bone. This is also significant in that often times, repair of hard tissue, such as bone, is accompanied by the need to repair soft tissue as well. One example is in the periodontal field where the presence of a material that would promote healing of the gums as well as the underlying bone would be advantageous. A patient having severe periodontal disease with significant bone loss could be treated using the bioactive hydrogel matrix of the present invention. The bioactive hydrogel matrix could be inserted into the area of bone loss and the gum tissue replaced over the area. The bioactive hydrogel matrix, through its interaction with stem or progenitor cells and subsequent changes in gene expression, as well as the other activities described above, would not only facilitate the regeneration of the bone, but also hasten the repair of the gum tissue overlying the injured bone. The same type of action would be expected to take place in other types of injury resulting in damage to bone as well as the surrounding tissue.

The present invention, in one aspect, is a method for regenerating connective tissue comprising administering a bioactive hydrogel matrix comprising a polypeptide and a long chain carbohydrate, as described herein, to a site in need of connective tissue regeneration. Preferentially, the polypeptide is a gelatin, and the long chain carbohydrate is dextran.

The bioactive hydrogel matrix as used in the method of the invention can include one or more of the additional components previously noted herein. Additionally, the bioactive hydrogel matrix can incorporate further components facilitating the regeneration of connective tissue according to the method of the invention.

According to another aspect, the present invention provides various connective tissue regenerative compositions. Generally, the compositions comprise a bioactive hydrogel matrix as described herein and at least one additional component useful for accomplishing the methods of the invention. Accordingly, any of the compositions described herein can be used in the various methods of the invention.

In one embodiment of the invention, the bioactive hydrogel matrix further comprises at least one osteoinductive or osteoconductive material. By "osteoinductive" is meant materials that lead to a mitogenesis of undifferentiated perivascular mesenchymal cells leading to the formation of osteoprogenitor cells (i.e., cells with the capacity to form new bone). By "osteoconductive" is meant materials that facilitate blood vessel incursion and new bone formation into a defined passive trellis structure. Various compounds, minerals, proteins, and the like are known to exhibit osteoinductive or osteoconductive activity. Accordingly, any of such materials would be useful according to the present invention.

In particular, any of the following could be used for their osteoinductive or osteoconductive ability according to the present invention: demineralized bone matrix (DBM), bone morphogenetic proteins (BMPs), transforming growth factors (TGFs), fibroblast growth factors (FGFs), insulin-like growth factors (IGFs), platelet-derived growth factors (PDGFs), epidermal growth factors (EGFs), vascular endothelial growth factors (VEGFs), vascular permeability factors (VPFs), cell adhesion molecules (CAMs), calcium aluminate, hydroxyapatite, coralline hydroxyapatite, alumina, zirconia, aluminum silicates, calcium phosphate, tricalcium phosphate, calcium sulfate, polypropylene fumarate, bioactive glass, porous titanium, porous nickel-titanium alloy, porous tantalum, sintered cobalt-chrome beads, ceramics, collagen, autologous bone, allogenic bone, xenogenic bone, coralline, and derivates or combinations thereof, or other biologically produced composite materials containing calcium or hydroxyapatite structural elements.

By "alumina" is meant the commonly held definition of materials comprised of the natural or synthetic oxide of aluminum, which may be exemplified in various forms, such as corundum. Bioactive glasses generally contain silicon dioxide ($SiO_2$) as a network former and are characterized by their ability to firmly attach to living tissue. Examples of bioactive glasses available commercially and their manufacturers include Bioglass® (American Biomaterials Corp., USA, 45% silica, 24% calcium oxide (CaO), 24.5% disodium oxide ($Na_2O$), and 6% pyrophosphate ($P_2O_5$)), Consil® (Xeipon Ltd., UK), NovaBone® (American Biomaterials Corp.), Biogran® (Orthovita, USA), PerioGlass® (Block Drug Co., USA), and Ceravital® (E. Pfeil & H. Bromer, Germany). Corglaes® (Giltech Ltd., Ayr, UK) represents another family of bioactive glasses containing pyrophosphate rather than silicon dioxide as a network former. These glasses contain 42-49 mole % of $P_2O_5$, the remainder as 10-40 mole % as CaO and $Na_2O$.

When present in the bioactive hydrogel matrix of the present invention, the osteoinductive or osteoconductive material is preferably present at a volume concentration of about 0.01 percent to about 90 percent based upon the total volume of the connective tissue regenerative composition. Such concentration is further dependent upon the ability to form compositions having suitable putty or paste-like properties. Preferably, the osteoinductive or osteoconductive material is present at a volume concentration of about 50 percent to about 80 percent, based upon the total volume of the connective tissue regenerative composition. In one particular embodiment, a composition according to the invention comprises a 75% volume/volume mixture of osteoinductive or osteoconductive material, such as calcium sulfate, and bioactive hydrogel matrix (e.g., 12 mL calcium sulfate to 4 mL hydrogel matrix).

As a connective tissue regenerative composition, the bioactive hydrogel matrix and the osteoinductive or osteoconductive materials can be variously combined. Preferably, the osteoinductive or osteoconductive materials and the hydrogel matrix are in admixture, which can be according to any means generally known to one of skill in the art. For example, the bioactive hydrogel matrix could be prepared, and the osteoinductive or osteoconductive material (e.g., powdered calcium phosphate) could be poured into and mixed into the hydrogel matrix by mechanical mixing means. The mixture could be flowable or could be substantially thickened to a putty or paste-like consistency. According to another embodiment, the bioactive hydrogel matrix could be dehydrated and, preferentially, in particulate or pelletized form. The particulate dehydrated bioactive hydrogel matrix could be mixed with an osteoinductive or osteoconductive material to form a substantially uniform mixture. In particular, the osteoinductive or osteoconductive material could be in the form of a putty or paste, and the particulate dehydrated bioactive hydrogel matrix kneaded or otherwise mixed therein.

In yet another embodiment of the invention, the bioactive hydrogel matrix of the invention can further comprise at least one medicament useful for treating patients having connective tissue damage or in need of connective tissue regeneration. The medicament can be any medicament useful in facilitating the healing and regenerative process. Such medicaments useful according to the invention include, but are not limited to, antivirals, antibacterials, anti-inflammatories, immunosuppressants, analgesics, anticoagulants, and wound healing promotion agents.

According to another embodiment of the invention, the bioactive hydrogel matrix can further comprise stem or progenitor cells, such as ADAS cells, which are known to be capable of differentiating into adipogenic, osteogenic, chondrogenic, and myogenic lineages. Accordingly, the presence of stem or progenitor cells can be beneficial for stimulating and increasing connective tissue regrowth, particularly bone and cartilage. Further, the presence of the stem or progenitor cells can be beneficial for stimulating and increasing growth of surrounding tissue, providing support for the damaged connective tissue. Preferably, stem or progenitor cells are present at a concentration of about 10,000 to about 1,000,000 cells per ml of hydrogel matrix, more preferably about 50,000 to about 750,000 cells per ml of hydrogel matrix, most preferably about 100,000 to about 500,000 cells per ml of hydrogel matrix. In one particular embodiment, the final concentration is about 250,000 cells per ml of hydrogel matrix. In a further embodiment of the invention, the bioactive hydrogel matrix includes stem cells and progenitor cells. In a particularly preferred embodiment, the progenitor cells are osteoprogenitor cells.

In one particular embodiment, the bioactive hydrogel matrix could be in a particulate, dehydrated form and the particles mixed into a solution containing stem or progenitor cells, such as ADAS or mesenchymal stem cells.

In another embodiment of the invention, the bioactive hydrogel matrix includes a three-dimensional structural framework. As previously noted, the bioactive hydrogel matrix of the present invention becomes flowable at physiological temperatures. As such, it is beneficial, in certain embodiments, for the bioactive hydrogel matrix to include structural components. Preferentially, the bioactive hydrogel matrix is at least partially contained within the three-dimensional structural framework. Accordingly, the structural framework can take on various embodiments.

In one particular embodiment, the three-dimensional structural framework includes a scaffold or cage-like structure at least partially containing the bioactive hydrogel matrix. Such an embodiment is particularly useful in areas of long segmental diaphyseal bone loss or bone cavitation, or in the spinal column. The scaffold or cage-like structure spans the area of bone loss and encloses the bioactive hydrogel matrix within the area of bone loss. For example, the three-dimensional structural framework could be a cylindrical metal mesh, such as titanium mesh. Accordingly, the three-dimensional structural framework can include materials that are non-bioreabsorbable (i.e., persist in the body in a virtually unchanged state or must be later removed). Advantageously, the three-dimensional structural framework includes a bioreabsorbable material that persists in the body long enough to perform its structure-providing function, later being broken down through natural body processes or being incorporated into the newly formed bone. In one particular embodiment, the three-dimensional structural framework includes calcium-containing or calcified materials easily incorporated into newly formed bone.

In another embodiment, the three-dimensional structural framework is at least partially internal to the bioactive hydrogel matrix. In such embodiments, the three-dimensional structural framework preferably comprises a material capable of physically or chemically interacting with the hydrogel matrix. Preferably, the three-dimensional structural framework provides an array of structural formations for providing support and structure to the bioactive hydrogel matrix.

It is particularly advantageous that the three-dimensional structural framework be a structure that provides support and simultaneously provides a space, or network of spaces, for cellular infiltration. It is particularly beneficial for the three-dimensional structural framework to include a porous structure, such as a collagen or gelatin sponge. Any commercially available collagen sponge would be useful generally in the present invention. Examples of commercially available collagen sponges include the Avitene Ultrafoam™ collagen sponge (available from Davol, Inc., a subsidiary of C. R. Bard, Inc., Murray Hill, N.J.—available online at http://www.davol.com), DuraGen® collagen sponge (available from Integra LifeSciences Corp., Plainsboro, N.J.), and Gelfoam®, a gelatin based sponge (available from Pharmacia & Upjohn, Kalamazoo, Mich.). Ceramic foams such as those produced by Hi-Por Ceramics (Sheffield, UK), could also be used.

The three-dimensional structural framework can be a single unit having an inherent three-dimensional structure. As such, the structural framework can be shaped as desired to precisely fit into the site in need of connective tissue regeneration. This is particularly beneficial in cases of long segmental diaphyseal bone loss or bone cavitation. In such cases, the structural framework can be precisely shaped and sized to the bone loss segment or cavitation to fill the space. The bioactive hydrogel matrix is retained in the bone loss segment or cavitation for an extended time period to facilitate bone regeneration by being at least partially contained within the structural framework. To further placement of the bioactive hydrogel matrix, the structural framework, with the hydrogel matrix contained therein, can optionally be sutured into place.

The three-dimensional structural framework can comprise various materials useful for providing structure and support and having an inherent three dimensional structure. The three-dimensional structural framework can be a structure substantially in the form as found in nature, such as coralline or natural sponge. Further, the three-dimensional structural framework can be a fabricated structure made from materials not naturally exhibiting a three-dimensional structure but being formed into such a structure, such as, for example, sintered calcium phosphate. Similarly, the three-dimensional structural framework can comprise one or more polymeric materials that have been made, through processing (such as casting, molding, or sintering), into a three-dimensional structure, particularly having a series or network of pores or cavities throughout the structure for allowing cellular infiltration. Examples of various materials useful as, or in the preparation of, a three-dimensional structural framework include, but are not limited to, metals, calcium salts, coralline, bioactive glass, sponges, ceramics, collagen, keratin, fibrinogen, alginate, chitosan, hyaluronan, and other biologically-derived polymers. The three-dimensional structural framework can also comprise degradable and non-degradable polymers, such as those commonly used in tissue engineering applications. Exemplary non-degradable polymers include polyethylene, poly(vinylidene fluoride), poly(tetrafluoroethylene), poly(vinyl alcohol), poly(hydroxyalkanoate), poly(ethylene terephthalate), poly(butylene terephthalate), poly(methyl methacrylate), poly(hydroxyethyl methacrylate), poly(N-isopropylacrylamide), poly(dimethyl siloxane), polydioxanone, and polypyrrole. Exemplary degradable polymers include poly(glycolic acid), poly(lactic acids), poly(ethylene oxides), poly(lactide-co-glycolides), poly(s-caprolactone), polyanhydrides, polyphosphazenes, poly(ortho-esters), and polyimides.

In one particularly preferred embodiment, the three-dimensional structural framework comprises a crosslinked hydrogel matrix. Particularly preferred is a crosslinked bioactive hydrogel matrix comprising a polypeptide, such as gelatin, and a long-chain carbohydrate, such as dextran. Published U.S. Patent Application No. 2003/0232746, which is incorporated herein by reference in its entirety, describes a crosslinked bioactive hydrogel matrix, wherein the hydrogel matrix of the present invention is further stabilized and imparted a three-dimensional type structure through crosslinking of the matrix components. Such crosslinked bioactive hydrogel matrix is also described in PCT Publication No. WO 03/072155, which is also incorporated herein by reference in its entirety. Additionally, Published U.S. Patent Application No. 2003/0232198 and PCT Publication No. WO 03/072157, both of which are also incorporated herein by reference in their entirety, describe a stabilized bioactive hydrogel matrix as a surface coating. Such crosslinked hydrogel matrices are also useful in the various additional embodiments of the present invention as described herein.

An example of a crosslinked bioactive hydrogel matrix comprising dextran and gelatin is provided in FIG. 8 wherein dextran 20 is covalently crosslinked to gelatin 15 by linkages 70, thereby forming a crosslinked network 50. The linkages 70 either result from reaction of functional groups on the gelatin 15 with functional groups on the dextran 20, or result from reaction of a bifunctional crosslinker molecule with both the dextran 20 and gelatin 15. As explained in greater detail below, one method of crosslinking gelatin and dextran is to modify the dextran molecules 20, such as by oxidation, in order to form functional groups suitable for covalent attachment to the gelatin 15. This stabilized crosslinked bioactive network 50 yields therapeutically useful gels and pastes that are insoluble in physiologic fluids at physiological temperatures.

Crosslinked hydrogel matrices as useful according to the present invention can be prepared by various methods. In one particular embodiment, one of the polypeptides and long chain carbohydrates is modified to form reactive groups suitable for crosslinking. For instance, the dextran or other long chain carbohydrate component can be modified, such as by oxidation, in order to cross-link with the polypeptide component. One known reaction for oxidizing polysaccharides is periodate oxidation. The basic reaction process utilizing periodate chemistry is well known and appreciated by those skilled in the art. Periodate oxidation is described generally in *Affinity Chromatography: A Practical Approach*, Dean, et al., IRL Press, 1985 ISBN0-904147-71-1, which is incorporated by reference in its entirety. The oxidation of dextran by the use of periodate-based chemistry is described in U.S. Pat. No. 6,011,008, which is herein incorporated by reference in its entirety.

In periodate oxidation, polysaccharides may be activated by the oxidation of the vicinal diol groups. With long chain carbohydrates, such as dextran, this is generally accomplished through treatment with an aqueous solution of a salt of periodic acid, such as sodium periodate ($NaIO_4$), which oxidizes the sugar diols to generate reactive aldehyde groups (e.g. dialdehyde residues). This method is a rapid, convenient alternative to other known oxidation methods, such as those using cyanogen bromide. Dextran activated by periodate oxidation may be stored at 4° C. for several days without appreciable loss of activity.

Long chain carbohydrate materials, such as dextran, activated in this manner readily react with materials containing amino groups, such as polypeptides, particularly gelatin, producing a crosslinked material through the formation of Schiff's base links. A Schiff base is a name commonly used to refer to the imine formed by the reaction of a primary amine with an aldehyde or ketone. The aldehyde groups formed on the cellulosic surface react with most primary amines between pH values from about 4 to about 6. The Schiff's base links form between the dialdehyde residues of the dextran and the free amino groups on the gelatin. The crosslinked product may subsequently be stabilized (i.e. formation of stable amine linkages) by reduction with a borohydride, such as sodium borohydride ($NaBH_4$) or sodium cyanoborohydride ($NaBH_3CN$). The residual aldehyde groups may be consumed with ethanolamine or other amine containing species to further modify the crosslinked matrix. Other methods known to those skilled in the art may be utilized to provide reactive groups on either one or both of the polypeptide and long-chain carbohydrate.

In preparing crosslinked bioactive hydrogel matrices for use in the present invention, periodate chemistry is preferentially used with dextran to form a multifunctional polymer that can then react with gelatin and other components, such as polar amino acids, present during the manufacturing process. The periodate reaction leads to the formation of polyaldehyde polyglycans that are reactive with primary amines. For example, polypeptides and long chain carbohydrates may form covalent hydrogel complexes that are colloidal or covalently crosslinked gels. Covalent bonding occurs between reactive groups of the dextran and reactive groups of the gelatin component. The reactive sites on the gelatin include amine groups provided by arginine, asparagine, glutamine, and lysine. These amine groups react with the aldehyde or ketone groups on the dextran to form a covalent bond. These hydrogels can be readily prepared at temperatures from about 34° C. to about 90° C. Additionally, the hydrogels can be prepared at a pH range of from about 5 to about 9, preferably from about 6 to about 8, and most preferably from about 7 to about 7.6.

By controlling the extent of dextran activation and the reaction time, one can produce stabilized biomimetic scaffolding materials of varying viscosity and stiffness. By "biomimetic" is intended compositions or methods imitating or simulating a biological process or product. Some biomimetic processes have been in use for several years, such as the artificial synthesis of vitamins and antibiotics. More recently, additional biomimetic applications have been proposed, including nanorobot antibodies that seek and destroy disease-causing bacteria, artificial organs, artificial arms, legs, hands, and feet, and various electronic devices. The biomimetic scaffolding materials of the present invention yield therapeutically useful gels and pastes that are stable at about 37° C., or body temperature. These gels are capable of expansion and/or contraction, but will not dissolve in aqueous solution. Accordingly, such biomimetic crosslinked hydrogel matrices are particularly useful as a three-dimensional structural framework as described herein. The crosslinked hydrogel matrix provides the structure and support required, remains stable and maintains its three-dimensional structure at physiological temperatures, and can beneficially provide many of the same connective tissue regenerative properties of the non-crosslinked bioactive hydrogel matrix of the invention.

As an alternate method for forming the crosslinked dextran/gelatin network, a multifunctional crosslinking agent may be utilized as a reactive moiety that covalently links the gelatin and dextran chains. Such bifunctional crosslinking agents may include glutaraldehyde, epoxides (e.g., bis-oxiranes), oxidized dextran, p-azidobenzoyl hydrazide, N-[α-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride, and other bifunctional crosslinking reagents known to those skilled in the art.

In another embodiment utilizing a crosslinking agent, polyacrylated materials, such as ethoxylated (20) trimethylpropane triacrylate, may be used as a non-specific photo-activated crosslinking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a crosslinked hydrogel network.

As with the non-crosslinked bioactive hydrogel matrix of the invention, the crosslinked hydrogel matrix can further comprise various additional components (in addition to the polypeptide and long chain carbohydrate) to enhance the crosslinked matrix by providing further stability or functional advantages. Such additional components can include any compound, especially polar compounds, that, when incorporated into the crosslinked hydrogel matrix, enhance the hydrogel matrix by providing further stability or functional advantages.

Preferred additional components for use with the stabilized crosslinked hydrogel matrix include polar amino acids, polar amino acid analogues and derivatives, intact collagen, and divalent cation chelators. Suitable concentrations of each particular preferred additional component are the same as noted above in connection with the bioactive hydrogel matrix of the present invention. Polar amino acids, EDTA, and mixtures thereof, are particularly preferred. The additional components can be added to the hydrogel matrix composition before or during the crosslinking of the polypeptide and long chain carbohydrate.

In one embodiment of the invention, the bioactive hydrogel matrix of the invention is in a crosslinked form, the three-dimensional structural framework thus being inherent to the hydrogel matrix itself. In another embodiment of the invention, the bioactive hydrogel matrix of the invention is first prepared, and the three-dimensional structural framework, in the form of a separate, crosslinked hydrogel matrix, as described above, is added to the non-crosslinked hydrogel matrix. Such addition can include physical admixture of the two hydrogels to form a composition comprising a bioactive hydrogel matrix of the invention and a three-dimensional structural framework, in the form of a crosslinked hydrogel matrix. In one particular embodiment, dehydrated crosslinked bioactive hydrogel matrix formulations can be used with the non-crosslinked hydrogel matrix or for providing structural support generally. In this embodiment, the non-crosslinked hydrogel matrix can be mixed with dehydrated crosslinked hydrogel matrix in the form of disks, rods, cylinders, granules, or other suitable geometric forms. Such compositions provide additional support to the surrounding tissue, and increase the localized residence time of the non-crosslinked hydrogel matrix.

Various embodiments of the invention can also be combined, particularly in preparing the various connective tissue regenerative compositions of the invention. For example, in one particular embodiment, the bioactive hydrogel matrix/three-dimensional structural framework composition could also include osteoinductive or osteoconductive materials, stem or progenitor cells (such as ADAS or mesenchymal stem cells), or medicaments as described herein. Furthermore, any of these combinations could be used according to the methods of the invention.

The methods of the invention wherein the bioactive hydrogel matrix includes a three-dimensional structural framework are intended to encompass situations wherein the three-dimensional structural framework is included with the bioactive hydrogel matrix prior to administration of the composition. Further, the methods encompass situations wherein the three-dimensional structural framework is included with the bioactive hydrogel matrix after administration of the bioactive hydrogel matrix.

The methods and compositions of the invention as described herein are useful in the repair and regeneration of connective tissue, particularly bone, cartilage, ligament, and the like. As such, the methods and compositions of the invention are particularly useful in various treatments involving portions of the human body particularly susceptible to connective tissue damage or degeneration.

According to one embodiment of the invention, the bioactive hydrogel matrix can be used in the surgical attachment or reattachment of one or more connective tissues. Because of the generally decreased vascularization of connective tissue types, healing times related to injury repair are typically long in duration. Administration of the bioactive hydrogel matrix to the injured site during repair of the connective tissue damage can improve integration of the tissues resulting in a much stronger repair and decreased healing time. This is particularly true in the reattachment of tendon or ligament to bone. Similar effects would be expected in the repair of torn ligaments or torn tendons.

Accordingly, the present invention provides a method for reattaching connective tissues to one another. The method generally comprises coating at least a portion of at least one of the connective tissues with the bioactive hydrogel matrix according to any of the various embodiments of the present invention, contacting the connective tissues, and, optionally, suturing the connective tissues together. Generally, suturing (or use of other attachment aids, such as staples, glues, and adhesive strips) is advisable when using the bioactive hydrogel matrix to maintain the connection between the connective tissues during healing and reduce occurrence of separation of the tissues prior to sufficient re-growth and reattachment of the connective tissues. In one particular embodiment, at least a portion of the bioactive hydrogel matrix can be in crosslinked form.

The improved repair/regeneration supplied by the bioactive hydrogel matrix would be beneficial to a large number of patients. While relatively moderate numbers of patients suffer from large areas of bone loss, the matrix could also be used to treat injuries that are very common in occurrence, such as a torn anterior cruciate ligament (ACL), rotator cuff injuries, damaged cartilage in knees and other joints, and other such injuries that would be readily obvious to one of ordinary skill in the art.

The bioactive hydrogel matrix of the invention further would be expected to be beneficial for improved performance of any bioreabsorbable tissue anchors. Accordingly, in a further embodiment of the invention, the bioactive hydrogel matrix, according to any of the various compositions described herein, could be used in a combination therapy with other known reattachment devices. For example a torn connective tissue, such as a tendon, could be reattached using sutures, staples, glues, or the like, with at least one piece of the torn connective tissue being coated at the area of the tear with a bioactive hydrogel matrix of the present invention to facilitate re-growth of connective tissue at the injury site and hasten reattachment of the connective tissue.

According to another embodiment of the invention, the matrix is useful in treating degenerative diseases, such as osteoarthritis, of the natural joint of a patient. Osteoarthritis is characterized by degeneration of the articular cartilage, hypertrophy of bone at the margins, and changes in the synovial membrane of the affected joint. Treatment of the affected joint with the bioactive hydrogel matrix of the invention, especially prior to complete loss of cartilage in the joint, can stabilize the progression of the degeneration and even promote repair/regeneration of cartilage within the joint and regeneration of marginal bone structure. Further, the bioactive hydrogel matrix of the invention provides an effective, minimally invasive treatment, the hydrogel matrix being capable of injection directly into the affected joint.

In this embodiment of the invention, the bioactive hydrogel matrix can be in many of the various compositions as provided herein. Advantageously, the bioactive hydrogel matrix further comprises one or more medicaments, osteoinductive or osteoconductive materials, or stem or progenitor cells.

In yet another embodiment of the invention, the bioactive hydrogel matrix is useful in promoting the healing and effectiveness of artificial joint replacements. According to this embodiment, the matrix is inserted into the area surrounding the artificial joint, particularly where the artificial joint is in contact with the natural tissue of the patient. The hydrogel matrix facilitates the integration of the artificial joint into the surrounding tissue promoting faster healing of the surgical site and greater duration of the effectiveness of the artificial joint.

Preferably, a therapeutic amount of the matrix of the invention is administered to a patient suffering from connective tissue injury, particularly an injury to bone, cartilage, tendon, or ligament. The patient can be any animal, including mammals such as dogs, cats and humans. The term "therapeutic amount" refers to the amount required to promote tissue repair/regeneration as evidenced by, for example, the formation of new bone tissue across an area previously lacking in bone tissue. The therapeutic amount will be primarily determined by the size and type of injury being treated. Typically, the volume of bioactive hydrogel matrix applied is about 1 to about 60 mL, but could be greater, especially in large injuries, such as, for example, an area of great bone loss in a large bone, such as a femur. Preferably, the therapeutic amount is sufficient to provide a uniform scaffolding for cellular attachment and differentiation in the area where tissue regeneration is needed. The non-crosslinked version of the hydrogel matrix is typically warmed to a temperature of about 35 to about 40° C. prior to administration in order to liquefy the matrix.

The bioactive hydrogel matrix used according to the methods of the present invention for regenerating connective tissue may be comprised solely of the polypeptide and long chain carbohydrate as described herein. Preferably, the hydrogel matrix may incorporate additional components, such as the polar amino acids, polar amino acid analogues and derivatives, and cation chelators, as described above. Table 1 below lists particularly preferred components of the matrix of the present invention along with suitable concentrations as well as preferred concentrations for each component. Note that the concentrations listed in Table 1 for gelatin and dextran would also be suitable for alternative polypeptide and long chain carbohydrate components. Bioactive hydrogel matrices prepared having the preferred components and concentrations provided in Table 1 would also be particularly suitable for use in the preparation of any of the connective tissue regenerative compositions as described herein.

TABLE 1

| Component | Concentration Range | Preferred Concentration |
| --- | --- | --- |
| L-glutamic acid | 2 to 60 mM | 20 mM |
| L-lysine | 0.5 to 30 mM | 5.0 mM |
| Arginine | 1 to 40 mM | 15 mM |
| Gelatin | 0.01 to 40 mM | 0.75 mM |
| L-cysteine | 5 to 5000 µM | 700 µM |
| L-alanyl-L-glutamine | 0.001 to 1 mM | 0.01 mM |
| EDTA | 0.01 to 10 mM | 4 mM |
| Dextran | 0.01 to 10 mM | 0.1 mM |
| Zinc | 0.005 to 3 mM | 0.03 mM |

EXPERIMENTAL

The present invention is more fully illustrated by the following examples, which are set forth to illustrate the present invention and are not to be construed as limiting thereof.

Example 1

Matrix Preparation

In one embodiment, the bioactive hydrogel matrix was compounded to yield a final formulation as described above in Table 1. Modified Medium 199 (2.282 L) was placed into a stirred beaker. To the beaker were added L-cysteine, L-glutamic acid, L-lysine, L-alanyl-L-glutamine, and EDTA. While stirring, the solution was heated to 50° C. Next, dextran was added, followed by the addition of gelatin. NaOH (10%) was used to adjust the pH of the matrix solution to a final pH of 7.50±0.05. Finally, additional L-glutamic acid, L-arginine, and L-cysteine were added followed by the addition of zinc sulfate. The amounts of each component used were the amounts necessary to bring the final concentration of each component to the preferred concentration provided in Table 1.

Example 2

Effect of Bioactive Hydrogel Matrix on Critical Size Defect in Bone

The in vivo effect of the matrix on bone repair was examined using the critical size defect model in the rabbit ulna. A defect in a rabbit ulna was created in which the length of the defect was purposefully made to be three times the diameter of the bone, i.e., a 15 mm defect was created in each ulna (the diameter of the bone was approximately 4 mm). It is well documented in the literature that defects of this size will not spontaneously heal (i.e., a critical size defect). Seven rabbits had 15 mm defects surgically created in the ulna of each forelimb. Further, the periosteum of the radius parallel to the defect was scraped off. In each rabbit, the defect in one forelimb was treated with the bioactive hydrogel matrix, and the other was treated with a collagen sponge soaked with the bioactive hydrogel matrix. The muscle surrounding the bone defect was sutured closed and the limb tightly wrapped.

The forelimbs of the rabbit were x-rayed to document the size of the defect, with follow-up X-rays taken at two-week intervals to 10 weeks of total testing. Micro CT scans and histological examination were also performed at 10 weeks. Radiographs of defect sites were scored for calcification on a 0 to 4 scale. Mineralization within the defect treated with the bioactive hydrogel matrix alone in combination with the collagen sponge was noted as early as two weeks after the procedure, and by six weeks, clear and dramatic mineralization was evident within the area of removed bone. The bioactive hydrogel matrix in the collagen sponge tended to increase calcification compared to the hydrogel matrix alone, but the differences were not statistically significant. New bone formation within the defects was confirmed by both micro CT scans and histopathology performed at 10 weeks.

Example 3

Effect of Bioactive Hydrogel Matrix on Tendon Re-growth and Strength

Four sheep had a 4 mm length of the central portion of the patellar tendon removed from the point of attachment of the tibia to the patella of one leg. A small block of the patella with the attached patellar tendon was also removed. The contralateral leg served as the unoperated control. Two defects were filled with a collagen sponge (DuraGen®, Integra Life-Sciences) infiltrated with the bioactive hydrogel matrix of the invention, and two defects were filled with a DuraGen® collagen sponge infiltrated with saline. The implants were sutured into the patellar tendon defect and surgical site was sutured closed. After 12 weeks, the patellar tendons were removed for gross observation and mechanical testing for stiffness. The tendons treated with the bioactive hydrogel matrix appeared thicker than the control tendons. Further, the tendons treated with the bioactive hydrogel matrix had an average increase in stiffness over the control tendons of about 17.2% compared to a decrease of 4.5% in stiffness of the 2 tendons treated with the collagen sponge soaked with saline.

Example 4

BMP-2 Gene Expression in Presence of Bioactive Hydrogel Matrix

Human osteosarcoma cells were plated in T75 flasks, allowed to grow to confluency, and then shifted to serum-free medium (SFM) for three days. At this point cultures were treated for 40 minutes at 37° C. with either the bioactive hydrogel matrix of the invention or serum-free medium as a control. Cultures were rinsed and re-fed with serum-free medium and sampled over a subsequent 24 hour period for extraction of nucleic acids. Messenger RNA from these preparations was used to create complementary DNA using reverse transcription, and specific DNA sequences were amplified and quantified using real-time polymerase chain reaction methods.

In several replicate experiments, induction of messenger RNA for bone morphogenetic protein-2 (BMP-2) was induced as much as 44-fold, with a peak response seen 2 hours after treatment with the bioactive hydrogel matrix with a return to baseline levels in 9 hours. Controls retained basal expression of the BMP-2 message over the entire 24 hour sampling period.

Expression of BMP-2 protein was also measured in these cell cultures following identical culture and hydrogel matrix treatment methods, with the exception that serum-containing medium (SCM) was used to avoid loss of analyte by adsorption to culture surfaces. For these studies cultures were sampled over a 3-day period following either 40 or 120-minutes treatment by removal of medium and snap freezing the culture to release cell-associated protein for analysis. Resulting samples were analyzed by enzyme-linked immunosorbent assay (ELISA) using a commercial BMP-2 detection kit (R&D Systems, Minneapolis, Minn.). In replicate studies, treatment with the bioactive hydrogel matrix increased BMP-2 protein levels over controls within 24 hours post-treatment and provided as much as a 3-fold increase over controls by day 3. These data are presented graphically in FIG. 9. These data demonstrate that the rapid increase in gene expression described earlier (FIG. 5) leads to a sustained increase in BMP-2 protein production.

Example 5

BMP-2 Gene Expression in Presence of Crosslinked Bioactive Hydrogel Matrix

Samples of crosslinked bioactive hydrogel matrix prepared with 1% oxidized dextran were cast into disks to fit into 24-well plates. Disks were sterilized in alcohol and equilibrated to culture medium and SAOS-2 human osteosarcoma cells were seeded at approximately 330,000 per disk. After allowing time for cell attachment, disks were transferred to new wells and sampled on days 1, 2, 3 and 6 for extraction of nucleic acids and quantitative PCR measurement of transcripts for BMP-2. Controls were seeded cells that settled past the disks and attached and grew on the bottom of the original wells used for disk seeding. These studies showed a rise in BMP-2 mRNA that reached a peak nearly 3.5-fold greater than initial levels by day 3 and remained elevated at day 6. The results are displayed graphically in FIG. 10.

Example 6

Preparation of Compositions Including Bioactive Hydrogel Matrix and Orthopedic Materials A putty containing 2.4 g calcium sulfate and 1.5 g demineralized bone matrix (DBM) was prepared and used to incorporate particulate dehydrated bioactive hydrogel matrix. After briefly hand-kneading the material, about 0.5 g of particulate dehydrated bioactive hydrogel matrix (equivalent to about 3 mL of fully hydrated hydrogel matrix) was incorporated into the putty. The putty was mixed and kneaded to uniformity, and the putty retained the ability to fill a bony defect created in a synthetic bone.

In a second composition, an injectable calcium sulfate formulation was prepared using the bioactive hydrogel matrix of the invention rather than the conventional water base (12 g calcium sulfate powder and 4 mL of the bioactive hydrogel matrix). The material had a prolonged set time (over 2 hours to solidify), and during the early stages of setting was judged to be suitable for filling a bony defect.

In a third composition, the bioactive hydrogel matrix was mixed with a granulated tricalcium phosphate ceramic to form a moldable putty easily packed into a bony defect.

Many modifications and other embodiments of the invention will come to mind to one skilled in the art to which this invention pertains having the benefit of the teachings presented in the foregoing descriptions and associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A connective tissue regenerative composition for administration at a site in need of connective tissue regeneration, the composition comprising:
    a) a bioactive hydrogel matrix that is flowable at physiological temperatures comprising:
        i. a tissue-derived polypeptide derived from tissue selected from the group consisting of collagens, gelatins, keratin, decorin, aggrecan, and glycoproteins, or a tissue-derived polypeptide derived from extracts of tissue selected from the group consisting of submucosal tissues, arteries, vocal chords, pleura, trachea, bronchi, pulmonary alveolar septa, ligaments, auricular cartilage, abdominal fascia, liver, kidney, neurilemma, arachnoid, dura mater, and pia mater,
        ii. a polysaccharide or a sulfated polysaccharide, and
        iii. one or more components selected from the group consisting of polar amino acids, divalent cation chelators, and combinations thereof; and
    b) a three-dimensional structural framework at least partially containing the bioactive hydrogel matrix and at least partially retaining the hydrogel matrix at the site in need of connective tissue regeneration, the structural framework providing support during connective tissue regeneration and simultaneously providing a space or network of spaces for cellular infiltration;
    wherein the three-dimensional structural framework is a crosslinked hydrogel formed of at least two polymers crosslinked to one another and that is solid or semi-solid at physiological temperatures, the crosslinked hydrogel comprising one or more components selected from the group consisting of polar amino acids, divalent cation chelators, and combinations thereof.

2. The composition of claim 1, wherein the tissue-derived polypeptide has a molecular mass of about 3,000 to about 3,000,000 Da.

3. The composition of claim 2 wherein the tissue-derived polypeptide has a molecular mass of about 30,000 to about 300,000 Da.

4. The composition of claim 1, wherein the polysaccharide or sulfated polysaccharide is a polysaccharide comprising more than about 10 monosaccharide residues joined to each other by glycosidic linkages.

5. The composition of claim 1, wherein the polysaccharide or sulfated polysaccharide is selected from the group consisting of glycosaminoglycans and glucosaminoglycans.

6. The composition of claim 1, wherein the polysaccharide or sulfated polysaccharide is a polysaccharide selected from the group consisting of dextran, heparan, heparin, hyaluronic acid, alginate, agarose, carageenan, amylopectin, amylose, glycogen, starch, cellulose, chitin, and chitosan.

7. The composition of claim 1, wherein the polysaccharide or sulfated polysaccharide is a sulfated polysaccharide selected from the group consisting of heparan sulfate, chondroitin sulfate, dextran sulfate, dermatan sulfate, and keratan sulfate.

8. The composition of claim 1, wherein the polysaccharide or sulfated polysaccharide has a molecular mass of about 2,000 to about 8,000,000 Da.

9. The composition of claim 8, wherein the polysaccharide or sulfated polysaccharide has a molecular mass of about 20,000 to about 1,000,000 Da.

10. The composition of claim 1, wherein the tissue-derived polypeptide is gelatin and the polysaccharide or sulfated polysaccharide is dextran.

11. The composition of claim 10, wherein the gelatin is skin-derived gelatin.

12. The composition of claim 10, wherein the gelatin is bone-derived gelatin.

13. The composition of claim 10, wherein the gelatin has a molecular mass of about 80,000 to about 200,000 Da.

14. The composition of claim 13, wherein the polydispersity of the molecular mass of the gelatin is about 1 to about 3.

15. The composition of claim 14, wherein the polydispersity of the molecular mass of the gelatin is about 1.1 to about 2.4.

16. The composition of claim 10, wherein the gelatin is present at a concentration of about 0.01 to about 40 mM.

17. The composition of claim 10, wherein the dextran has a molecular mass of about 300,000 to about 600,000 Da.

18. The composition of claim 17, wherein the polydispersity of the molecular mass of the dextran is 1 to about 3.

19. The composition of claim 18, wherein the polydispersity of the molecular mass of the dextran is about 1.1 to about 2.4.

20. The composition of claim 10, wherein the dextran is present at a concentration of about 0.01 to about 10 mM.

21. The composition of claim 1, wherein the bioactive hydrogel matrix that is flowable at physiological temperatures further comprises at least one polar amino acid selected from the group consisting of tyrosine, cysteine, serine, threonine, asparagine, glutamine, aspartic acid, glutamic acid, arginine, lysine, histidine, and mixtures thereof.

22. The composition of claim 21, wherein the polar amino acids are present at a concentration of about 3 to about 150 mM.

23. The composition of claim 21, wherein the polar amino acids are present at a concentration of about 10 to about 65 mM.

24. The composition of claim 21, wherein the polar amino acids are selected from the group consisting of L-cysteine, L-glutamic acid, L-lysine, L-arginine, and mixtures thereof.

25. The composition of claim 21, wherein the bioactive hydrogel matrix comprises L-glutamic acid at a concentration of about 2 to about 60 mM.

26. The composition of claim 21, wherein the bioactive hydrogel matrix comprises L-lysine at a concentration of about 0.5 to about 30 mM.

27. The composition of claim 21, wherein the bioactive hydrogel matrix comprises L-arginine at a concentration of about 1 to about 40 mM.

28. The composition of claim 21, wherein the bioactive hydrogel matrix comprises L-cysteine at a concentration of about 0.005 to about 5 mM.

29. The composition of claim 1, wherein the bioactive hydrogel matrix that is flowable at physiological temperatures further comprises ethylenediaminetetraacetic acid or a salt thereof.

30. The composition of claim 29, wherein the ethylenediaminetetraacetic acid or salt thereof is present at a concentration of about 0.01 to about 10 mM.

31. The composition of claim 1, further comprising at least one osteoinductive or osteoconductive material.

32. The composition of claim 31, wherein the at least one osteoinductive or osteoconductive material is selected from the group consisting of demineralized bone matrix (DBM), bone morphogenetic proteins (BMPs), transforming growth factors (TGFs), fibroblast growth factors (FGFs), insulin-like growth factors (IGFs), platelet-derived growth factors (PDGFs), epidermal growth factors (EGFs), vascular endothelial growth factors (VEGFs), and vascular permeability factors (VPFs).

33. The composition of claim 1, wherein the crosslinked hydrogel comprises a polypeptide crosslinked to a long chain carbohydrate and wherein the long chain carbohydrate is a polysaccharide or a sulfated polysaccharide.

34. The composition of claim 33, wherein the polypeptide of the crosslinked hydrogel is a tissue-derived polypeptide derived from tissue selected from the group consisting of collagens, gelatins, keratin, decorin, aggrecan, and glycoproteins.

35. The composition of claim 33, wherein the polysaccharide or sulfated polysaccharide is selected from the group consisting of dextran, heparan, heparin, hyaluronic acid, alginate, agarose, carageenan, amylopectin, amylose, glycogen, starch, cellulose, chitin, chitosan, heparan sulfate, chondroitin sulfate, dextran sulfate, dermatan sulfate, and keratan sulfate.

36. The composition of claim 33, wherein the polypeptide is gelatin and the polysaccharide is dextran or oxidized dextran.

37. The composition of claim 1, wherein the crosslinked hydrogel is at least partially dehydrated.

* * * * *